(12) United States Patent
Low et al.

(10) Patent No.: US 11,185,505 B2
(45) Date of Patent: Nov. 30, 2021

(54) DELIVERY OF AGENTS TO INFLAMED TISSUES USING FOLATE-TARGETED LIPOSOMES

(71) Applicant: PURDUE RESEARCH FOUNDATION, West Lafayette, IN (US)

(72) Inventors: Philip Stewart Low, West Lafayette, IN (US); Scott Poh, Lafeyette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 16/894,287

(22) Filed: Jun. 5, 2020

(65) Prior Publication Data
US 2020/0297632 A1 Sep. 24, 2020

Related U.S. Application Data

(62) Division of application No. 13/700,358, filed as application No. PCT/US2011/038437 on May 27, 2011, now abandoned.

(60) Provisional application No. 61/349,434, filed on May 28, 2010.

(51) Int. Cl.
| | | |
|---|---|---|
| *A61K 9/127* | (2006.01) | |
| *A61K 49/00* | (2006.01) | |
| *A61K 51/12* | (2006.01) | |
| *A61K 47/55* | (2017.01) | |
| *A61K 47/69* | (2017.01) | |
| *A61K 9/00* | (2006.01) | |
| *A61K 31/573* | (2006.01) | |
| *A61B 5/055* | (2006.01) | |
| *A61B 6/00* | (2006.01) | |
| *A61B 8/08* | (2006.01) | |

(52) U.S. Cl.
CPC ............ *A61K 9/127* (2013.01); *A61K 9/00* (2013.01); *A61K 9/1271* (2013.01); *A61K 31/573* (2013.01); *A61K 47/551* (2017.08); *A61K 47/6911* (2017.08); *A61K 49/0032* (2013.01); *A61K 49/0043* (2013.01); *A61K 49/0054* (2013.01); *A61K 51/1234* (2013.01); *A61B 5/055* (2013.01); *A61B 6/481* (2013.01); *A61B 8/481* (2013.01)

(58) Field of Classification Search
CPC .. A61K 9/127; A61K 9/1271; A61K 49/0043; A61K 51/1234; A61K 49/0032; A61K 47/551; A61K 47/6911; A61K 9/00; A61K 31/573; A61K 49/0054; A61B 5/055; A61B 6/481; A61B 8/481; A61P 29/00
See application file for complete search history.

(56) References Cited

U.S. PATENT DOCUMENTS

| | | |
|---|---|---|
| 4,721,612 A | 1/1988 | Janoff et al. |
| 6,056,973 A | 5/2000 | Allen et al. |
| 6,316,024 B1 | 11/2001 | Allen et al. |
| 6,852,334 B1 | 2/2005 | Cullis et al. |
| 2002/0192157 A1 | 12/2002 | Low et al. |
| 2003/0026831 A1 | 2/2003 | Lakkaraju |
| 2006/0204565 A1 | 9/2006 | Low et al. |
| 2007/0009434 A1 | 1/2007 | Low et al. |
| 2007/0041934 A1 | 2/2007 | William et al. |
| 2009/0214636 A1 | 8/2009 | Low et al. |
| 2009/0226509 A1 | 9/2009 | Metselaar |
| 2009/0311191 A1 | 12/2009 | Annapragada et al. |
| 2011/0237686 A1 | 9/2011 | Ng et al. |
| 2014/0179761 A1 | 6/2014 | Manoharan et al. |

FOREIGN PATENT DOCUMENTS

| | | |
|---|---|---|
| EP | 06628201 | 5/1997 |
| JP | 62052188 | 3/1987 |
| WO | 1997/07466 | 4/1994 |
| WO | 1997/31624 | 9/1997 |
| WO | 03/105805 | 12/2003 |

OTHER PUBLICATIONS

International Search Report for PCT/US11/038437 dated Sep. 22, 2011.
Lee et al., Folate-Targeted Liposomes for Drug Delivery. Journal of Liposome Research. 1997, vol. 7(4), p. 455-466.
Lee and Low, Folate-mediated tumor cell targeting of liposome-entrapped doxorubicin in vitro. Biochimica et Biophysica Acta 1233 (1995) 134-144; 11 pages.
Rayburn et al., Mol. Cell Pharmacol. 2009; 1(1): 29-43.
Al-Muhammad et al., J. Microencapsulation, 1996, vol. 13, No. 2, 123-130.

(Continued)

*Primary Examiner* — Robert S Cabral
(74) *Attorney, Agent, or Firm* — Barnes & Thornburg LLP

(57) ABSTRACT

The invention described herein pertains to folate-receptor targeted agents comprising therapeutic agents useful for the treatment of inflammatory disease, including folate-receptor targeted liposomes (folate-targeted liposomes) containing entrapped therapeutic agents and folate-receptor targeted dendrimers conjugated to therapeutic agents (folate-targeted dendrimer conjugates), useful for the treatment of inflammatory disease, including auto-immune disease, as well as to folate-targeted liposomes containing entrapped imaging agents and dendrimer conjugates conjugated to imaging agents, for use in the diagnosis and monitoring of treatment in such disease.

18 Claims, 24 Drawing Sheets

(56) References Cited

OTHER PUBLICATIONS

Turk et al. Folate-conjugated liposomes preferentially target macrophages associated with ovarian carcinoma. Cancer letters (2004) 213:165-172.
Turk et al. Folate-targeted imaging of activated macrophages in rats with adjuvant-induced arthritis. Arthritis & Rheumatism (2002) 46(7): 1947-1955.
Nakashima-Matsushita et al. Selective expression of folate receptor beta and its possible role in methotrexate transport in synovial macrophages from patients with rheumatoid arthritis. Arthritis & Rheumatism (1999) 42(8): 1609-1616.
Lee and Low. Delivery of liposomes into cultured KB cells via folate receptor-mediated endocytosis. Journal of Biological Chemistry (1994) 269(5): 3198-3204.
Low and Antony. Folate receptor-targeted drugs for cancer and inflammatory diseases. Advanced Drug Delivery Reviews, (2004) 56(8): 1055-1058.
Turk et al. Extended Abstracts: Folate-mediated targeting of liposomes to tumor cells and Mac-1 expressing cells in-vivo. Journal of Controlled Release (2001) 74: 369-376.

A

B

C

NT LIPOSOME     FOL-LIPOSOME     HEALTHY

DELIVERY OF AGENTS TO INFLAMED TISSUES USING FOLATE-TARGETED LIPOSOMES

CROSS-REFERENCE TO RELATED APPLICATIONS

This application is a divisional of U.S. patent application Ser. No. 13/700,358, filed Nov. 27, 2012, which is a national stage entry under 35 USC § 371 of International Application No. PCT/US2011/038437, filed May 27, 2011, which claims the benefit of U.S. provisional application 61/349,434, filed 28 May 2010, each of which is incorporated by reference herein.

TECHNICAL FIELD

The invention described herein pertains to folate-receptor targeted agents comprising therapeutic agents useful for the treatment of inflammatory disease, including folate-receptor targeted liposomes (folate-targeted liposomes) containing entrapped therapeutic agents and folate-receptor targeted dendrimers conjugated to therapeutic agents (folate-targeted dendrimer conjugates), useful for the treatment of inflammatory disease, including auto-immune disease, as well as to folate-targeted liposomes containing entrapped imaging agents and dendrimer conjugates conjugated to imaging agents, for use in the diagnosis and monitoring of treatment in such disease.

BACKGROUND AND SUMMARY OF THE INVENTION

Liposomes are closed, spherical vesicles comprising amphiphilic lipids such as phospholipids, sphingolipids, and/or other lipids, including sterols such as cholesterol and cholesterol ester salts, in proportions such that they arrange themselves into multiple concentric bilayers when hydrated in aqueous solutions. Using any of a number of methods, such liposomes can be converted into single bilayer liposomes. These single bilayer liposomes are useful carriers both of hydrophilic (lipophobic) agents, which can reside entrapped in the aqueous interior of the liposome, and of hydrophobic (lipophilic) agents, which can reside entrapped in the lipid bilayer. The utility of liposomes as carriers for therapeutic agents has been recognized and has lead to the development of long-circulating liposomes. By altering the composition of the lipid bilayer in such liposomes by, for example, the inclusion of a surface coat of flexible biocompatible hydrophilic chains, the resulting liposomes have improved stability. The surface coat serves to protect the liposome from uptake by organs of the mononuclear phagocyte system, especially the liver, lung and spleen, and from the plasma components which are involved in liposome uptake. One example of the hydrophilic chain constituent of the surface coat is polyethylene glycol (PEG), in which the terminal hydroxy group may be capped with a methyl group to form a methyl ether group (denoted as mPEG or MPEG). (Unless specifically defined otherwise, in this specification PEG will include the hydroxy terminated form, the methyl ether terminated form, and any other similarly terminated form in the context of the surface coat of a liposome.)

Inflamed tissue regions in the body have been imaged using folate-targeted imaging agents. For example, the folate-receptor targeted, radionuclide conjugate imaging agent EC20 (folate-Tc99m), has been used to image rheumatoid arthritis sites in vivo.

In WO 94/07466 there is disclosed a PEG coated liposomal composition containing an entrapped therapeutic agent for concentrating therapeutics in an inflamed tissue region in the body. The beneficial effects of the liposomes of WO 94/07466 (EP-0662820) are questioned in WO 03/105805, which discloses PEG-coated liposomes composed of non-charged vesicle-forming lipids, optionally containing not more than 5 mol percent of charged vesicle-forming lipids, and containing a water soluble corticosteroid for the site-specific treatment of inflammatory disorders.

In a folate receptor positive mouse model of ovarian cancer, folate-targeted liposomes carrying the entrapped fluorescent dye calcein have been shown to unload the dye in ovarian cancer cells and tumor-associated macrophages within tumor ascites fluid associated with an intraperitoneal cancer both ex vivo and after in vivo administration and collection of the ascites fluid for analysis. (M. J. Turk et al., *Cancer Letters* 213 (2004) 165-172.) The same reference discloses folate targeted liposomes in which the lipid phase includes tritiated cholesterol-oleoyl ether.

Disclosed herein are folate-targeted liposomal compositions comprising an anti-inflammatory agent as an entrapped agent, pharmaceutical compositions comprising such liposomal compositions, and the use of such compositions in the treatment of an inflammatory disease, such as in an inflamed tissue region in the body. Entrapped agents can be encapsulated within the aqueous interior of the liposomes and/or dissolved into the hydrocarbon regions of their bilayers. Also disclosed are folate-targeted liposomal compositions comprising an imaging or visualizing agent as an entrapped agent, as well as the use of such liposomal compositions for diagnosis or monitoring the treatment of an inflammatory disease in an inflamed tissue region in the body.

Further disclosed herein are dendrimers conjugated to active agents (folate-targeted dendrimer conjugates), such as anti-inflammatory agents, pharmaceutical compositions comprising such dendrimer conjugates, and the use of such compositions in the treatment of disease such as inflammatory disease. Dendrimers are known classes of compounds which are generally regarded as repeatedly branched, approximately spherical molecules and are sometimes referred to as arborols or cascade molecules. Also, disclosed are folate-targeted dendrimer conjugate compositions comprising an imaging or visualizing agent, as well as the use of such compositions for diagnosis or monitoring the treatment of a disease such as inflammatory disease in an inflamed tissue region in the body.

Figure 24:

FIG. 24 shows the imaging of (the intestines of) mice in an intestinal inflammation model using imaging with a folate-targeted dendrimer conjugate conjugated to Cy5.5 dye (FolDend(G3)Cy5.5), with a non-targeted dendrimer conjugate conjugated to Cy5.5 dye, and in competition with a folate-targeted dendrimer conjugate which lacks a conjugated dye (FolDend(G3)Cy5.5 W Competion).

DETAILED DESCRIPTION

In one embodiment, there is provided a folate-receptor targeted agent comprising a therapeutic agent useful for the treatment of inflammatory disease. In one embodiment, the folate-receptor targeted agent is a folate-targeted liposomal composition comprising an anti-inflammatory agent as an entrapped agent. In one embodiment, the folate-receptor targeted agent is a folate-targeted dendrimer conjugate comprising a folate-targeted dendrimer conjugated to an anti-inflammatory agent.

In one embodiment, there is provided a folate-targeted liposomal composition comprising an anti-inflammatory agent as an entrapped agent. In general, the embodiment of the liposome may be as described herein or of any conventional composition and may be constructed as described herein or by any conventional methodology with the folate-targeting ligand attached as described herein or by any conventional linkage structure or methodology.

The lipid components used in forming the embodiments of the liposomes may be any of the variety of vesicle-forming lipids, including phospholipids, sphingolipids, and/or other lipids, including sterols such as cholesterol and cholesterol ester salts. Suitable lipids for the embodiments include those having two hydrocarbon chains, typically acyl chains, and a polar head group, such as phospholipids and glycolipids. As used herein, unless otherwise defined or clear from the context, phospholipid includes any one phospholipid or combination of phospholipids capable of forming liposomes. Phospholipids include phosphatidylcholines (PC), phosphatidylethanolamine (PE), phosphatidic acid (PA), phosphatidylinositol (PD), and sphingomyelin (SM), where the two hydrocarbon chains are typically between about 14-22 carbons in length, and have varying degrees of unsaturation. The glycolipids include cerebrosides and gangliosides. Phosphatidylcholines, including those obtained from natural sources or those that are partially or wholly synthetic, or of variable chain length and unsaturation, are suitable. Phospholipids which contain saturated alkyl chains, yielding a relatively high transition temperature, are suitable for the embodiments. These include, for example, distearoylphosphatidylethanolamine (DSPE), distearoylphosphatidylcholine (DSPC) and hydrogenated soy phosphatidylcholine (HSPC). One embodiment of the liposomal composition disclosed herein is one wherein the lipid bilayer is primarily composed of DSPC/cholesterol with a mol ratio of about 56:40.

The folate-targeting components used in forming the embodiments of the liposomes may be any of those known in the preparation of folate-targeted liposomes or those described herein. For examples of the preparation of folate-targeted liposomal compositions, see, for example, R. J. Lee et al., *J. Biological Chemistry*, 269(5) (1994) 3198-3204; and R. J. Lee et al., *Biochimica et Biophysica Acta*, 1233 (1995) 134-144.

One embodiment is a liposomal composition as described herein wherein the lipid bilayer comprises a comprises a folate targeting conjugate composed of (a) a lipid having a polar head group and a hydrophobic tail, (b) a hydrophilic polymer having a first end and a second end, said polymer attached at its first end to the head group of the lipid, and (c) a folate ligand (Fol) attached to the second end of the polymer, and wherein the folate ligand is a folic acid residue or an analog or derivative thereof. Folic acid analogs or derivatives thereof include the (unnatural) D-isomer of folic acid and derivatives other related folic acid receptor binding molecules, such as folinic acid, pteroic acid, pteropolyglutamic acid, receptor-binding pteridines such as tetrahydropterins, dihydrofolates, tetrahydrofolates, and their deaza and dideaza analogs. The terms "deaza" and "dideaza" analogs refer to the art-recognized folate analogs having a carbon atom substituted for one or two nitrogen atoms in the naturally occurring folic acid structure. Other folate analogs or derivatives include the folate receptor-binding analogs aminopterin, amethopterin (methotrexate), and derivatives thereof.

For example, in one embodiment, the hydrophilic polymer of the folate targeting conjugate is a PEG having an average molecular weight of about 200-5000 in which the end groups, prior to attachment, are independently amino, hydroxy, thiol or carboxy. In one embodiment the hydrophilic polymer of the folate targeting conjugate is a PEG having an average molecular weight of about 3200-3400 in which the end groups, prior to attachment, are independently amino or thiol. In one embodiment the hydrophilic polymer of the folate targeting conjugate is a PEG having an average molecular weight of about 3200-3400 in which the end groups, prior to attachment, are each amino, such as for example, $NH_2PEG_{3200}NH_2$ or $NH_2PEG_{3400}NH_2$, which also may be denoted as a polyoxyethylene bis-amine or a PEG bis-amine, such as for example PEG bis-amine, $M_r$ ~3350. In another embodiment, the hydrophilic polymer of the folate targeting conjugate is a PEG having an average molecular weight of about 3200-3400 in which the end groups, prior to attachment, are amino and thiol, which also may be denoted amino-PEG-SH. An amino-PEG-SH may be obtained from the corresponding PEG bis-amine by a conventional method, such as by the addition of Traut's reagent.

In one embodiment, the folate-targeted liposomal composition, the lipid having a polar head group and a hydrophobic tail, is a phosphatidyl group as defined herein. In one embodiment, the phosphatidyl group comprises two saturated acyl groups each of which is between about 14-22 carbons in length. In one embodiment, the phosphatidyl group comprises two saturated acyl groups each of which is between about 16-18 carbons in length. In one embodiment, the phosphatidyl group is a distearoyl (DS) derivative.

In the folate targeting conjugate the polar head group of the lipid is attached to the first end of the hydrophilic polymer by any conventional method. In one embodiment, the polar head group is part of a phosphatidylethanolamine, wherein the phosphatidyl group has any of the meanings herein, and the amino group of the ethanolamine portion is linked to an amino group of the first end of the hydrophilic polymer by a bis-acyl group, such as a succinyl group. A succinyl group also may be denoted as a 1,4-dioxobutane-1,4-diyl group. In another embodiment, the polar head group is part of a phosphatidylethanolamine, wherein the phosphatidyl group has any of the meanings herein, and the amino group of the ethanolamine portion is linked to a thiol group of the first end of the hydrophilic polymer via addition of the thiol group to an N-maleiimidocaproylphospatidylethanolamine. In one embodiment of any of the above, the phosphatidylethanolamine is distearoylphosphatidylethanolamine (DSPE).

In one embodiment of the folate-targeted liposomal composition, the folate ligand is a folic acid residue which is attached to an amino group at the second end of the hydrophilic polymer by acylation with the α-carbonyl group or the γ-carbonyl group of the glutamic acid portion of folic acid. In another embodiment of the folate-targeted liposomal composition, the folate ligand is a folic acid residue which is attached to an amino group at the second end of the hydrophilic polymer by acylation with the γ-carbonyl group of the glutamic acid portion of folic acid.

In one embodiment of the folate-targeted liposomal composition, the folate targeting conjugate comprises distearoylphosphatidylethanolamine linked to the first end of a bis-amino PEG and a folic acid residue which is attached to the amino group at the second end of the bis-amino PEG by acylation with the γ-carbonyl group of the glutamic acid portion of folic acid. In a further embodiment, the distearoylphosphatidylethanolamine is linked to the first end of the bis-amino PEG by a succinyl group.

A further embodiment of the above liposomal composition is one wherein the folate targeting conjugate comprises distearoylphosphatidylethanolamine wherein the amino group of the ethanolamine portion is linked by a succinyl group to the amino group of the first end of a PEG having an average molecular weight of about 3200-3400 in which the end groups, prior to attachment, are each amino, and wherein the folate ligand is a folic acid residue which is attached to the amino group at the second end of the PEG by acylation with the γ-carbonyl group of the glutamic acid portion of folic acid.

In one embodiment of the folate-targeted liposomal composition, as described herein, the folate targeting conjugate is present at about 0.01 mol % to about 1 mol % in the lipid bilayer. In another embodiment, the folate targeting conjugate is present at about 0.05 mol % to about 0.5 mol % in the lipid bilayer. In another embodiment, the folate targeting conjugate is present at about 0.1 mol % in the lipid bilayer.

One embodiment is a liposomal composition as described herein wherein the lipid bilayer further comprises a hydrophilic coating composed of (a) a lipid having a polar head group and a hydrophobic tail and (b) a hydrophilic polymer having a first end and a second end, said polymer attached at its first end to the head group of the lipid and optionally capped at its second end. The hydrophilic coating components used in forming the embodiments of the liposomes may be any of those known in the preparation of hydrophilic coated liposomes or those described herein.

In general, the lipid of the hydrophilic coating having a polar head group and a hydrophobic tail can be any of those disclosed herein for the preparation of a folate targeting conjugate. Thus, in one embodiment, the lipid having a polar head group and a hydrophobic tail is a phosphatidyl group as defined herein. In one embodiment, the phosphatidyl group comprises two saturated acyl groups each of which is between about 14-22 carbons in length. In one embodiment, the phosphatidyl group comprises two saturated acyl groups each of which is between about 16-18 carbons in length. In one embodiment, the phosphatidyl group is a distearoyl (DS) derivative.

The hydrophilic polymer of the hydrophilic coating can be any of a number of biocompatible hydrophilic polymers. In one embodiment, the hydrophilic polymer is a polyethylene glycol (PEG), a polylactic acid (PLA), a polyglycolic acid (PGA) or a polyvinyl alcohol (PVA), as well as copolymers of lactic and glycolic acids, in which the first end group, prior to attachment, is amino, hydroxy or thiol. The hydrophilic polymer is optionally capped with methyl, ethyl, or another unreactive group. In another embodiment, the hydrophilic polymer is a polyethylene glycol with an average molecular weight of about 2000, which is uncapped or capped with a methyl or ethyl group.

The polar head group of the lipid is attached to the first end of the hydrophilic polymer of the hydrophilic coating by any conventional method. In one embodiment, the polar head group is part of a phosphatidylethanolamine, wherein the phosphatidyl group has any of the meanings herein, and the amino group of the ethanolamine portion is linked directly to a carbon of the first end of the hydrophilic polymer, or via a linker to an amino, hydroxy or thiol group of the first end of the hydrophilic polymer by a linking group. The amino group of the ethanolamine portion may be linked directly to a carbon of the first end of the hydrophilic polymer, for example by converting a hydroxy group to a leaving group, such as a triflate, and alkylating the amino group of the ethanolamine. The amino group of the ethanolamine portion of a phosphatidylethanolamine may be linked to a hydroxy group of the first end of the hydrophilic polymer, for example, by a linking group such as a carbonyl group or a 4-chloro-1,3,5-triazinyl group; or the amino group of the ethanolamine portion may be linked to an amino group of the first end of the hydrophilic polymer, for example, by a linking group such as a carbonyl group, a succinyl group or a 4-chloro-1,3,5-triazinyl group. The amino group of the ethanolamine portion of a phosphatidylethanolamine may be linked to a thiol group of the first end of the hydrophilic polymer by formation of a disulfide bond between an alkyl thiol group on the amino group of the ethanolamine and the thiol group of the hydrophilic polymer. For the preparation of a hydrophilic coating in which the hydrophilic polymer is not capped, the group at the second end may be protected using a conventional protecting group while the first end is attached to the polar head group of the lipid of the hydrophilic coating having a polar head group and a hydrophobic tail; then the protecting group is removed. For example, a hydroxy group at the second end of the hydrophilic polymer may be protected using a trimethylsilyl group, which is removed following the attachment of the first end of the hydrophilic polymer to the polar head group.

One embodiment is a liposomal composition as described herein wherein the lipid bilayer further comprises a hydrophilic coating comprising distearoylphosphatidyl-ethanolamine and polyethylenegycol 2000 ($PEG_{2000}$) or methoxypolyethyleneglycol 2000 ($mPEG_{2000}$).

One embodiment is a liposomal composition as described herein wherein the hydrophilic coating is present at about 1 to 20 mol % in the lipid bilayer. Another embodiment is a liposomal composition as described herein wherein the hydrophilic coating is present at about 4 mol % in the lipid bilayer.

One embodiment is a liposomal composition as described herein wherein the liposome bilayer comprises a mol ratio of DSPC/cholesterol/mPEG2000-DSPE of about 56:40:4. Another embodiment is a liposomal composition as described herein wherein the liposome bilayer comprises a mol ratio of DSPC/Chol/$mPEG_{2000}$-DSPE/Fol-$PEG_{3400}$DSPE of about 56:40:4:0.1.

One embodiment is a liposomal composition as described herein wherein the average particle size of the liposome is about 30 to 200 nM. Another embodiment is a liposomal composition as described herein wherein the average particle size of the liposome is about 40 to 120 nM. A further embodiment is a liposomal composition as described herein wherein the average particle size of the liposome is about 50 to 100 nM.

A further embodiment of folate-targeted liposomal compositions, as described herein, is the ability to deliver more of the entrapped agent to an inflamed site than corresponding non-targeted liposomal compositions, which are the same as the folate-targeted liposomal compositions, except the folate targeting conjugate, such as folate-PEG-DSPE, is omitted.

One embodiment is a liposomal composition, or folate-targeted dendrimer conjugate, as described herein wherein the entrapped anti-inflammatory agent is an anti-inflammatory steroid. In one embodiment, the anti-inflammatory steroid is a sytemically administered (lipophilic) anti-inflammatory steroid. In one embodiment, the anti-inflammatory steroid is betamethasone, dexamethasone, flumethasone, methylprednisolone, paramethasone, prednisolone, prednisone, triamcinolone, hydrocortisone or cortisone. A further embodiment is a liposomal composition as described herein wherein the entrapped agent is betamethasone.

In another embodiment, the anti-inflammatory steroid is a topically administered anti-inflammatory steroid. In this sense, topically administered includes administration by any of a number of nonsystemic means, including by inhalation, suppository, topical cream ointment, foam, lotion or gel, etc. In one embodiment, the anti-inflammatory steroid is alcomethasone dipropionate, amcinonide, betamethasone dipropionate, betamethasone monopropionate, betamethasone 17-valerate, budesonide, budesonide disodium phosphate, ciclomethasone, clobetasol-17-propionate, clobetasone-17-butyrate, cortisone acetate, deprodone propionate, desonide, desoxymethasone, dexamethasone acetate, diflucortolone valerate, diflurasone diacetate, diflucortolone, difluprednate, flumetasone pivalate, flunisolide, fluocinolone acetonide acetate, fluocinonide, fluocortolone, fluocortolone caproate, fluocortolone hexanoate, fluocortolone pivalate, fluormetholone acetate, fluprednidene acetate, fluticasone propionate, halcinonide, halometasone, hydrocortisone acetate, hydrocortisone-17-butyrate, hydrocortisone-17-valerate, medrysone, methylprednisolone acetate, mometasone furoate, parametasone acetate, prednicarbate, prednisolone acetate, prednylidene, rimexolone, tixocortol pivalate, triamcinolone acetonide, triamcinolone alcohol or triamcinolone hexacetonide. In one embodiment, the anti-inflammatory steroid is budesonide, flunisolide or fluticasone propionate.

In another embodiment, the anti-inflammatory steroid is a water soluble anti-inflammatory steroid. Another embodiment is a liposomal composition as described herein wherein the anti-inflammatory steroid is betamethasone sodium phosphate, desonide sodium phosphate, dexamethasone sodium phosphate, hydrocortisone sodium phosphate, hydrocortisone sodium succinate, cortisone sodium phosphate, cortisone sodium succinate, methylprednisolone disodium phosphate, methylprednisolone sodium succinate, methylprednisone disodium phosphate, methylprednisone sodium succinate, prednisolone sodium phosphate, prednisolone sodium succinate, prednisone sodium phosphate, prednisone sodium succinate, prednisolamate hydrochloride, triamcinolone acetonide disodium phosphate or triamcinolone acetonide dipotassium phosphate. In one embodiment, the anti-inflammatory steroid is budesonide disodium phosphate.

One embodiment is a liposomal composition, or folate-targeted dendrimer conjugate, as described herein wherein the entrapped anti-inflammatory agent is a non-steroidal anti-inflammatory drug (NSAID), which also may be denoted as a non-steroidal anti-inflammatory agent (NSAIA) or as a non-steroidal anti-inflammatory medicine (NSAIM). In one embodiment, the NSAID comprises a propionic acid derivative such as, for example, ibuprofen, naproxen, fenoprofen, ketoprofen, flurbiprofen or oxaprozin. In one embodiment, the NSAID comprises an acetic acid derivative, such as, for example, indomethacin, sulindac, etodolac or diclofenac. In one embodiment, the NSAID comprises an oxicam derivative, such as, for example, piroxicam, meloxicam, tenoxicam, droxicam, lomoxicam or isoxicam. In one embodiment, the NSAID comprises a fenamic acid derivative, such as, for example, mefenamic acid, meclofenamic acid, flufenamic acid or tolfenamic acid. In one embodiment, the NSAID comprises a selective COX-2 (cyclooxygenase-2) inhibitor (coxib), such as, for example, celecoxib, rofecoxib, valdecoxib, parecoxib, lumiracoxib or etoricoxib.

Another embodiment is a liposomal composition, or folate-targeted dendrimer conjugate, as described herein wherein the entrapped anti-inflammatory agent comprises another drug useful in the treatment of rheumatoid arthritis or other autoimmune disease including an antiproliferative, immunomodulator or immunosuppresant agent, comprising, for example, aspirin, methotrexate, sulfasalazine, D-penicillamine, nambumetone, aurothioglucose, auranofin, other gold-containing compound, colloidal gold, cyclosporin, tacrolimus, pimecrolimus or sirolimus.

Because liposomes are useful carriers both of hydrophilic, lipophobic agents, which can reside entrapped in the aqueous interior of the liposome, and of hydrophobic, lipophilic agents, which can reside entrapped in the lipid bilayer, it is possible to load a lipsome as disclosed herein simultaneously with more than one anti-inflammatory agent, any of which may be hydrophilic or lipophilic. Similarly, it is possible to load a lipsome as disclosed herein simultaneously with an anti-inflammatory agent and a further therapeutic agent, any of which may be hydrophilic or lipophilic. Thus, one embodiment is a liposomal composition as described herein comprising more than one anti-inflammatory agent as an entrapped agent. Another embodiment is a liposomal composition as described herein wherein there are two entrapped anti-inflammatory agents. A further embodiment is a liposomal composition as described herein comprising an anti-inflammatory agent and a further therapeutic agent.

As a further embodiment, there is provided a pharmaceutical composition comprising a liposomal composition comprising an anti-inflammatory agent as an entrapped agent, or folate-targeted dendrimer conjugate, as described herein and further comprising at least one pharmaceutically acceptable carrier or excipient. The pharmaceutical composition may be formulated in a conventional manner as known for the formulation of liposomes for administration to patients. For example, the pharmaceutical composition may be a sterile dispersion in a buffered aqueous vehicle, optionally containing a tonicity adjusting agent. Alternatively, for example, the pharmaceutical composition may be a sterile, non-pyrogenic lyophilized product comprising a buffer and/or a tonicity adjusting agent, which is suitable for reconstitution with sterile water for injection to form a sterile dispersion. In either case, the sterile dispersion may diluted in 5% dextrose to an appropriate concentration prior to intravenous infusion. A pharmaceutical composition includes a veterinary composition.

As a further embodiment, there is provided a liposomal composition comprising an anti-inflammatory agent as an entrapped agent, or folate-targeted dendrimer conjugate, as described herein for use as a medicament. As a further embodiment, there is provided a liposomal composition comprising an anti-inflammatory agent as an entrapped agent, or folate-targeted dendrimer conjugate, as described herein for use in the treatment of an inflammatory disease. As a further embodiment, there is provided the use of a liposomal composition comprising an anti-inflammatory agent as an entrapped agent, or folate-targeted dendrimer conjugate, as described herein for the treatment of an inflammatory disease. As a further embodiment, there is provided the use of a liposomal composition comprising an anti-inflammatory agent as an entrapped agent, or folate-targeted dendrimer conjugate, as described herein for the manufacture of a medicament for the treatment of an inflammatory disease.

As a further embodiment, there is provided a method of treatment of an inflammatory disease in a subject in need thereof, comprising administering an effective amount of a liposomal composition comprising an anti-inflammatory agent as an entrapped agent, or folate-targeted dendrimer conjugate, as described in any of claims. In one embodiment the subject is a mammal. In one embodiment the subject is a human.

For any of the above uses or methods of treatment, in one embodiment the inflammatory disease comprises an inflamed tissue region in the body. In one embodiment the use or method is one wherein the inflammatory disease is arthritis, arteriosclerosis, graft-versus-host disease, multiple sclerosis, osteomyelitis, psoriasis or inflammatory bowel disease, such as Crohn's disease or ulcerative colitis. In one embodiment the use or method one wherein the inflammatory disease is arthritis. In one embodiment the use or method one wherein the inflammatory disease is rheumatoid arthritis. In one embodiment the use or method one wherein the inflammatory disease is osteoarthritis. In one embodiment the use or method one wherein the inflammatory disease is arteriosclerosis. In one embodiment the use or method one wherein the inflammatory disease is atherosclerosis. In one embodiment the use or method one wherein the inflammatory disease is inflammatory bowel disease, such as Crohn's disease or ulcerative colitis.

One embodiment is the use of a folate-targeted liposomal composition, or folate-targeted dendrimer conjugate, comprising an imaging or visualizing agent as an entrapped agent for diagnosis or monitoring the treatment of an inflammatory disease in an inflamed tissue region in the body. Another embodiment is the use of a folate-targeted liposomal composition, or folate-targeted dendrimer conjugate, comprising an imaging or visualizing agent as an entrapped agent for the manufacture of an agent for diagnosis or monitoring the treatment of an inflammatory disease in an inflamed tissue region in the body. Another embodiment is an agent for diagnosis or monitoring the treatment of an inflammatory disease, comprising a folate-targeted liposomal composition, or folate-targeted dendrimer conjugate, comprising an imaging or visualizing agent as an entrapped agent. Another embodiment is a pharmaceutical composition comprising a folate-targeted liposomal composition, or folate-targeted dendrimer conjugate, comprising an imaging or visualizing agent as an entrapped agent and further comprising at least one pharmaceutically acceptable carrier or excipient. A further embodiment is a method of using a folate-targeted liposomal composition, or folate-targeted dendrimer conjugate, comprising an imaging or visualizing agent as an entrapped agent for diagnosis or monitoring the treatment of an inflammatory disease in an inflamed tissue region in the body in a subject in need thereof. One embodiment of the method is wherein the subject is a mammal. Another embodiment of the method is wherein the subject is a human.

For any use, agent, pharmaceutical composition or method of using a folate-targeted liposomal composition wherein the entrapped agent is a folate-targeted liposomal composition comprising an imaging or visualizing agent, other than the difference in the entrapped agent, embodiments of the folate-targeted liposomal composition may be characterized in the same manner as embodiments of a folate-targeted liposomal composition comprising an anti-inflammatory agent as an entrapped agent as described herein. Similarly for folate-targeted dendrimer conjugates comprising an imaging or visualizing agent, embodiments may be characterized in the same manner as embodiments comprising an anti-inflammatory agent.

One embodiment of the above use, agent, pharmaceutical composition or method is one wherein the entrapped or conjugated agent is a pharmaceutically acceptable fluorescent dye. In one embodiment, the fluorescent dye is DiD (1,1'-dioctadecyl-3,3,3',3'-tetramethyl-indodicarbocyanine perchlorate), calcein or fluorescein.

Another embodiment of the above use, agent, pharmaceutical composition or method is one wherein the entrapped or conjugated agent is a contrast agent for X-ray, MRI (magnetic resonance imaging) or ultrasound. One embodiment is the X-ray contrast agent is iobitridol.

Another embodiment of the above use, agent, pharmaceutical composition or method is one wherein the entrapped or conjugated agent comprises a radionuclide. In one embodiment, the radionuclide is an isotope of gallium, indium, copper, technitium or rhenium. In another embodiment, the radionuclide is an isotope of technitium.

One embodiment comprises a kit comprising a folate-targeted liposomal composition, or folate-targeted dendrimer conjugate, comprising an imaging or visualizing agent as an entrapped agent as described herein and instructions for diagnosis or monitoring the treatment of an inflammatory disease.

As described above, a folate-targeted liposomal composition comprising the fluorescent dye calcein has been described. (M. J. Turk et al., *Cancer Letters* 213 (2004) 165-172.) However, a folate-targeted liposomal composition comprising an imaging or visualizing agent other than a fluorescent dye as an entrapped agent provides a novel embodiment. For a folate-targeted liposomal composition comprising an imaging or visualizing agent other than a fluorescent dye as an entrapped agent, embodiments of the folate-targeted liposomal composition may be characterized in the same manner as embodiments of a folate-targeted liposomal composition comprising an anti-inflammatory agent as an entrapped agent as described herein.

In one embodiment the folate-targeted liposomal composition, or folate-targeted dendrimer conjugate, comprising an imaging or visualizing agent other than a fluorescent dye as an entrapped agent is one wherein the entrapped agent is an X-ray contrast agent. In one embodiment, the X-ray contrast agent is iobitridol.

In another embodiment the folate-targeted liposomal composition, or folate-targeted dendrimer conjugate, comprising an imaging or visualizing agent other than a fluorescent dye as an entrapped agent is one wherein the entrapped agent comprises a radionuclide. In one embodiment, the radionuclide is an isotope of gallium, indium, copper, technitium or rhenium. In one embodiment, the radionuclide is an isotope of technitium.

One embodiment is a pharmaceutical composition comprising a liposomal composition, or folate-targeted dendrimer conjugate, comprising an imaging or visualizing agent other than a fluorescent dye as an entrapped agent and further comprising at least one pharmaceutically acceptable carrier or excipient. Another embodiment is the use of a folate-targeted liposomal composition, or folate-targeted dendrimer conjugate, comprising an imaging or visualizing agent other than a fluorescent dye as an entrapped agent for diagnosis or monitoring the treatment of an inflammatory disease in an inflamed tissue region in the body. Another embodiment is the use of a folate-targeted liposomal composition, or folate-targeted dendrimer conjugate, comprising an imaging or visualizing agent other than a fluorescent dye as an entrapped agent for the manufacture of an agent for diagnosis or monitoring the treatment of an inflammatory disease in an inflamed tissue region in the body. Another embodiment is an agent for diagnosis or monitoring the treatment of an inflammatory disease, comprising a folate-targeted liposomal composition, or folate-targeted dendrimer conjugate, comprising an imaging or visualizing agent other than a fluorescent dye as an entrapped agent. A further embodiment is a method of using a folate-targeted liposomal composition, or folate-targeted dendrimer conjugate, comprising an imaging or visualizing agent other than a fluorescent dye as an entrapped agent for diagnosis or monitoring the treatment of an inflammatory disease in an inflamed tissue region in the body in a subject in need thereof. One embodiment of the method is wherein the subject is a mammal. Another embodiment of the method is wherein the subject is a human.

An embodiment is a kit comprising a folate-targeted liposomal composition, or folate-targeted dendrimer conjugate, comprising an anti-inflammatory agent as an entrapped agent, or a pharmaceutical composition thereof, as described herein, and an imaging agent for the inflammatory condition. In one embodiment of the kit, the imaging agent is a folate-targeted imaging agent. In another embodiment of the kit, the folate-targeted imaging agent is a folate-targeted liposomal composition, or folate-targeted dendrimer conjugate, as described herein. In a further embodiment of the kit, the folate-targeted imaging agent is a folate-targeted conjugate of an imaging agent. In one embodiment of the kit, the folate-targeted conjugate is EC20 (folate-Tc99m).

An additional embodiment of any of the above described kits is a kit further comprising instructions for diagnosis or monitoring the treatment of an inflammatory disease. An additional embodiment of any of the above described kits is a kit further comprising instructions for the treatment of an inflammatory disease.

Embodiments of the invention are further described by the following enumerated clauses:

1. A folate-receptor targeted agent comprising a therapeutic agent useful for the treatment of inflammatory disease.

2. The folate-receptor targeted agent of clause 1 which is a folate-targeted liposomal composition comprising an anti-inflammatory agent as an entrapped agent.

3. The liposomal composition of clause 2 wherein the lipid bilayer is primarily composed of DSPC/cholesterol with a mol ratio of about 56:40.

4. The liposomal composition of clause 2 or 3 wherein the lipid bilayer comprises a comprises a folate-targeting conjugate composed of (a) a lipid having a polar head group and a hydrophobic tail, (b) a hydrophilic polymer having a first end and a second end, said polymer attached at its first end to the head group of the lipid, and (c) a folate ligand (Fol) attached to the second end of the polymer, and wherein the folate ligand is a folic acid residue or an analog or derivative thereof.

5. The liposomal composition of clause 4 wherein the hydrophilic polymer of the folate targeting conjugate is a PEG having an average molecular weight of about 200-5000 in which the end groups, prior to attachment, are independently amino, hydroxy, thiol or carboxy.

6. The liposomal composition of any of clauses 2-5 wherein the folate targeting conjugate is present at about 0.01 mol % to about 1 mol % in the lipid bilayer.

7. The liposomal composition of any of clauses 4-6 wherein the lipid bilayer further comprises a hydrophilic coating composed of (a) a lipid having a polar head group and a hydrophobic tail and (b) a hydrophilic polymer having a first end and a second end, said polymer attached at its first end to the head group of the lipid and optionally capped at its second end.

8. The liposomal composition of clause 7 wherein the hydrophilic coating is a polyethylene glycol (PEG), a polylactic acid (PLA), a polyglycolic acid (PGA) or a polyvinyl alcohol (PVA).

9. The liposomal composition of clause 7 or 8 wherein the hydrophilic polymer is a polyethylene glycol with an average molecular weight of about 2000, which is uncapped or capped with a methyl or ethyl group.

10. The liposomal composition of any of clauses 2-9 wherein the entrapped agent is an anti-inflammatory steroid.

11. The liposomal composition of any of clauses 2-10 wherein the entrapped agent is a drug useful in the treatment of rheumatoid arthritis or other autoimmune disease including an antiproliferative, immunomodulator or immunosuppresant agent.

12. A method of treatment of an inflammatory disease in a subject in need thereof, comprising administering an effective amount of a liposomal composition as described in any of clauses 2-12.

13. A pharmaceutical composition comprising a liposomal composition comprising an anti-inflammatory agent as an entrapped agent as described in any of clauses 2-12 and further comprising at least one pharmaceutically acceptable carrier or excipient.

14. A composition comprising a folate-targeted liposomal composition comprising an imaging or visualizing agent as an entrapped agent and further comprising at least one pharmaceutically acceptable carrier or excipient.

15. A method of using a folate-targeted liposomal composition comprising an imaging or visualizing agent as an entrapped agent for diagnosis or monitoring the treatment of an inflammatory disease in an inflamed tissue region in the body in a subject in need thereof.

16. A kit comprising a folate-targeted liposomal composition comprising an imaging or visualizing agent as an entrapped agent as described in clause 14 and instructions for diagnosis or monitoring the treatment of an inflammatory disease.

17. A kit comprising a folate-targeted liposomal composition comprising an anti-inflammatory agent as an entrapped agent, as described in any of clauses 2-11, or a pharmaceutical composition thereof, as described in clause 13, and an imaging agent for the inflammatory condition.

18. The folate-receptor targeted agent of clause 1 which is a folate-targeted dendrimer conjugate comprising a folate-targeted dendrimer conjugated to an anti-inflammatory agent.

19. The folate-targeted dendrimer conjugate of clause 18 wherein the dendrimer comprises a folate-targeting conjugate wherein the folate-targeting ligand (Fol) is a folic acid residue or an analog or derivative thereof, a hydrophilic coating, and a conjugated anti-inflammatory agent.

20. The folate-targeted dendrimer conjugate of clause 19 wherein the folate targeting conjugate is present at about 12-25% of the dendrimeric termini; the hydrophilic coating residue is present at about 25-40% of the dendrimeric termini; and the conjugated to anti-inflammatory agent is present at about 3-13% of the dendrimeric termini.

21. The folate-targeted dendrimer conjugate of clause 19 or 20 wherein the hydrophilic coating is a polyethylene glycol (PEG), a polylactic acid (PLA), a polyglycolic acid (PGA) or a polyvinyl alcohol (PVA).

22. The liposomal composition of any of clauses 19-21 wherein the hydrophilic polymer is a polyethylene glycol with an average molecular weight of about 2000, which is uncapped or capped with a methyl or ethyl group.

23. The folate-targeted dendrimer conjugate of any of clauses 19-22 wherein the conjugated anti-inflammatory agent is an anti-inflammatory steroid.

24. The folate-targeted dendrimer conjugate of any of clauses 19-23 wherein the conjugated anti-inflammatory agent is a drug useful in the treatment of rheumatoid arthritis or other autoimmune disease including an antiproliferative, immunomodulator or immunosuppresant agent.

25. A method of treatment of an inflammatory disease in a subject in need thereof, comprising administering an effective amount of a folate-targeted dendrimer conjugate as described in any of clauses 18-24.

26. A pharmaceutical composition comprising a folate-targeted dendrimer conjugate comprising an anti-inflammatory agent as described in any of clauses 18-24 and further comprising at least one pharmaceutically acceptable carrier or excipient.

27. A composition comprising a folate-targeted dendrimer conjugate comprising an imaging or visualizing agent as a conjugated agent and further comprising at least one pharmaceutically acceptable carrier or excipient.

28. A method of using a folate-targeted dendrimer conjugate comprising an imaging or visualizing agent as a conjugated agent for diagnosis or monitoring the treatment of an inflammatory disease in an inflamed tissue region in the body in a subject in need thereof.

29. A kit comprising a composition comprising a folate-targeted dendrimer conjugate comprising an imaging or visualizing agent as a conjugated agent as described in clause 27 and instructions for diagnosis or monitoring the treatment of an inflammatory disease.

30. A kit comprising a folate-targeted dendrimer conjugate comprising an anti-inflammatory agent as described in clause 18-24, or a pharmaceutical composition thereof, as described in clause 26, and an imaging agent for the inflammatory condition.

Exemplary preparations of folate-targeted liposomal compositions comprising an anti-inflammatory agent or an imaging agent as an entrapped agent, as well as exemplary preparations of the corresponding non-folate-targeted liposomal compositions, are provided below in the examples.

Arteriosclerosis has traditionally been viewed to simply reflect the deposition of lipids within the vessel wall of medium-sized and large arteries. Upregulation of cell adhesion molecules facilitates adherence of leukocytes to the dysfunctional endothelium and their subsequent transmigration into the vessel wall. Evolving inflammatory reaction results in the initiation of atherosclerotic plaques. A large number of recent studies demonstrate that activated macrophages constitute the key effector cells in atherosclerosis; and it was reported that the folate receptor, $FR_\beta$, the non-epithelial isoform of the folate receptor is expressed on activated (but not resting) macrophages.

Figure 14:
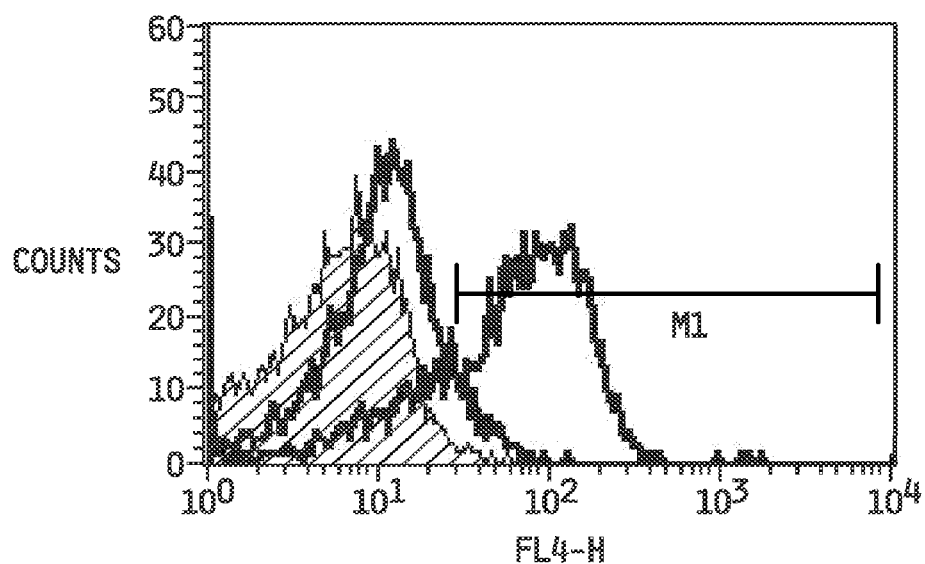
FIG. 14 shows the cell bound fluorescence measured by flow cytometry in thioglycolate recruited macrophages for control non-targeted calcein-entrapped liposomal compositions (shaded curve), and for folate-targeted calcein-entrapped liposomal compositions in the presence (middle curve) and absence (right curve) of excess free folic acid.

That the instant folate-targeted liposomal composition can deliver its entrapped agent to inflammation induced activated macrophages is demonstrated in Imaging Example 1, below. In that example the uptake of calcein from a calcein-entrapped folate-targeted liposomal composition by cells from rat peritoneal fluid in vitro is demonstrated in a thioglycolate-induced inflammation model using flow cytometry (FIG. 14). The calcein uptake is competitively inhibited by incubation in the presence of excess folic acid; and the comparable nontargeted (NT) liposomal composition delivers significantly less calcein. Because the dye within the liposomes is quenched at high concentration, the fluorescence is observed only following endocytosis and calcein unloading inside the target cells. Accordingly, such imaging experiments support the unloading of therapeutic agents in similar situations.

Apo E mice with the knock out mutation show a marked increase in total plasma cholesterol levels that are unaffected by age or sex. Fatty streaks in the proximal aorta are found at 3 month of age. The lesions increase with age and progress to lesions with less lipid but more elongated cells, typical of a more advanced stage of pre-atherosclerotic lesions. At 24 weeks of age, mice fed a normal diet show obvious atherosclerotic lesions in the aortic sinus and the ascending aorta. The number of atherosclerotic lesions in the aortic sinus and the ascending aorta is significantly increased in homozygotes fed an atherosclerotic western diet vs a normal diet.

Imaging Example 2 demonstrates the increased uptake of $^3$H-cholesterol labeled folate-targeted liposomes in the aorta and hearts of mice fed a high fat western diet compared to a normal diet, indicating the increase in atherosclerotic lesions in the western diet animal.

Imaging Examples 3 through 6 demonstrate the ability of folate-targeted liposomal compositions to deliver entrapped imaging agents to atherosclerotic sites in an atherosclerosis model employing Apo E knock out (Apo E KO) mice. Therapeutic Examples 1 and 2 demonstrate the ability of betamethasone-entrapped folate-targeted liposomal compositions to reduce the evidence of atherosclerotic inflammation in Apo E KO mice.

In Imaging Example 3, ability of a folate-targeted liposomal composition, with the entrapped fluorescent dye DiD, to label the atherosclerotic sites in Apo E KO mice fed a western diet for one week before dosing is demonstrated along with the competitive blocking of the labeling by pre-administered free folic acid. Imaging of both the whole animals (FIG. 2) and the excised aortic arch (FIG. 3) show the labeling of the sites and competitive blocking.

Imaging Example 4 (FIG. 4) provides a similar example in Apo E KO mice fed a western diet for four weeks before imaging under four conditions: (A) control with no imaging agent, (B) DiD-entrapped folate-targeted liposomal composition, (C) non-targeted DiD-entrapped liposomal composition, and (D) DiD-entrapped folate-targeted liposomal composition administered with an excess of folic acid. The images of the mice of each of the four treatment groups demonstrate superior uptake of the dye from the DiD-entrapped folate-targeted liposomal composition compared to the non-targeted DiD-entrapped liposomal composition, as well as the competitive inhibition of uptake of the dye from the DiD-entrapped folate-targeted liposomal composition by excess folic acid.

Figure 5:
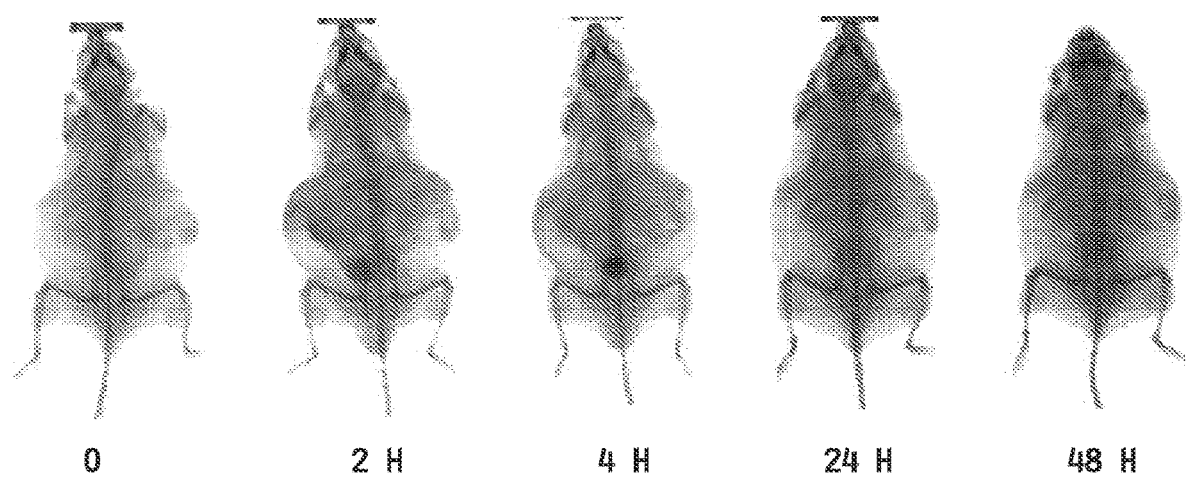
FIG. 5 shows radiographic (X-ray) imaging at preinjection (0) and 2, 4, 24 and 48 hours post injection of an Apo E KO mouse dosed with an iobitridol-entrapped folate-targeted liposomal composition.

Imaging Example 5 provides an example of an Apo E KO mouse dosed with an iobitridol-entrapped folate-targeted liposomal composition which demonstrates the use of an entrapped CT agent for radiographic imaging (FIG. 5).

Imaging Example 6 provides an example using radioisotopic imaging in Apo E KO mice fed a western diet for four weeks before dosing using a $^{99}$Tc-entrapped folate-targeted liposomal composition, administered either alone or with an excess of folic acid (FIG. 6), demonstrating the competitive blockage of uptake of the folate-targeted liposomal composition by excess folic acid.

Figure 8:
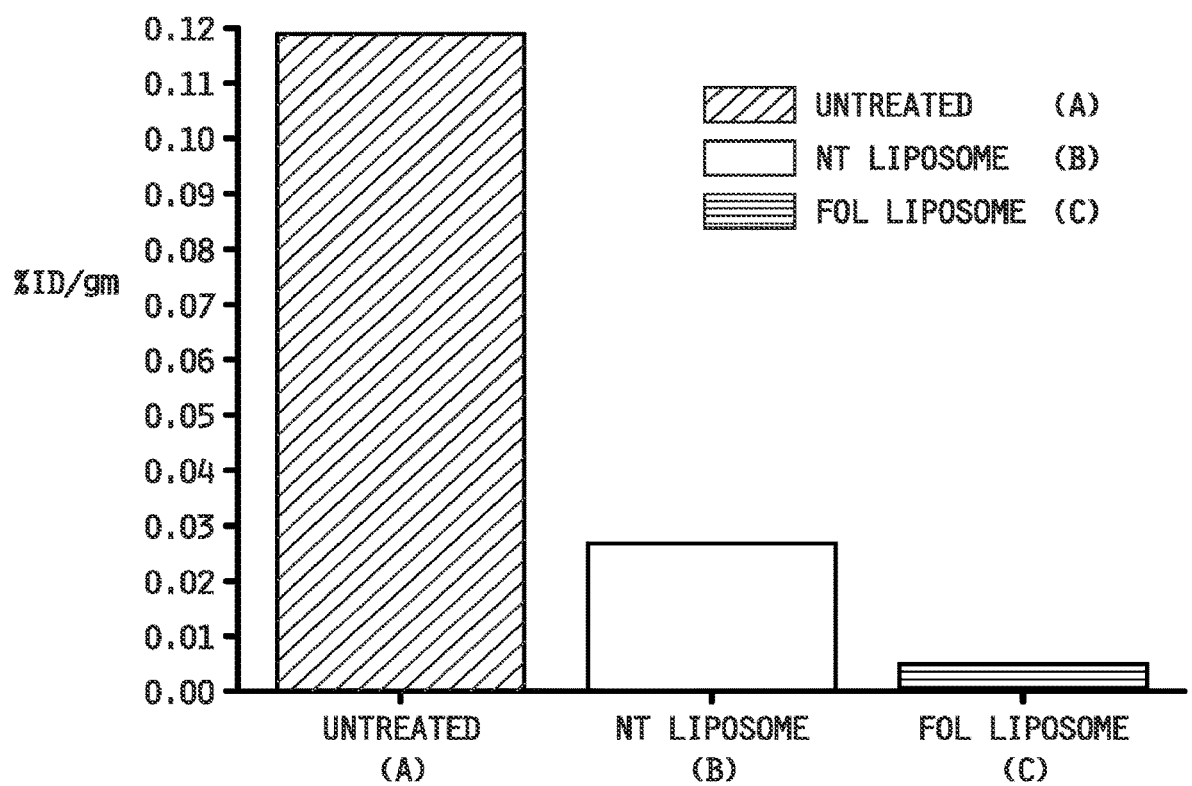
FIG. 8 shows the relative EC20 heart uptake of the groups of FIG. 7.
Figure 9:
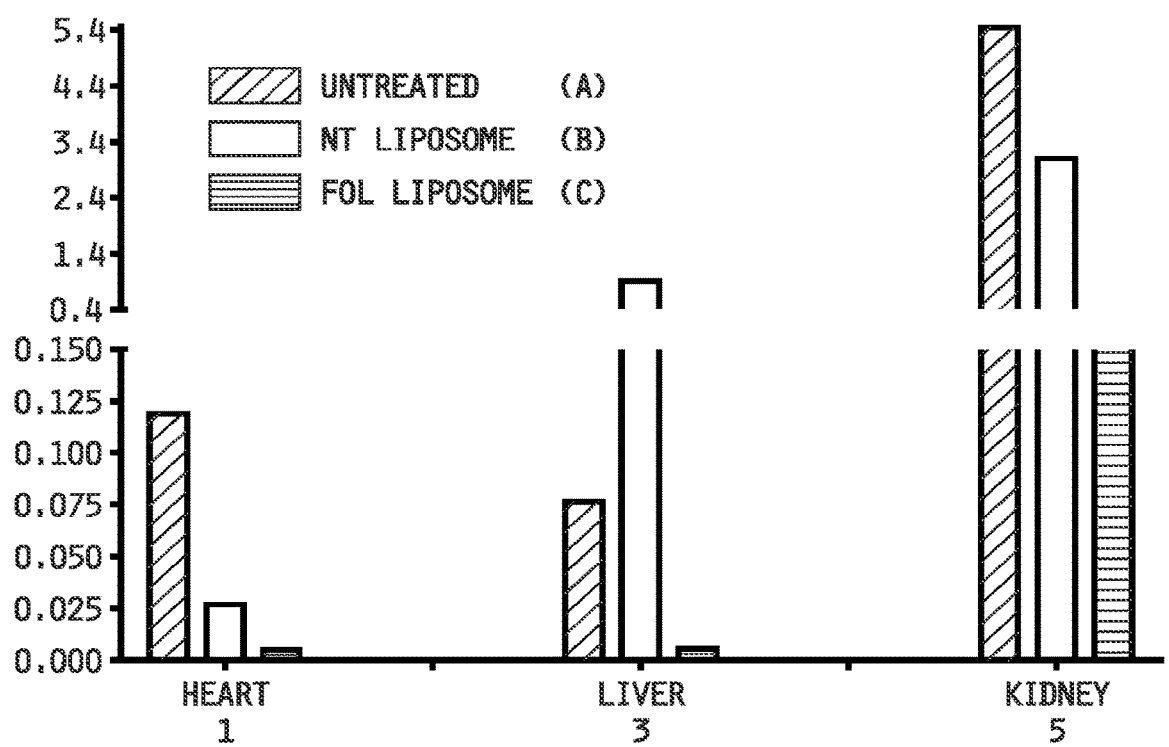
FIG. 9 shows the biodistribution of EC20 uptake in the organs (heart (1), lung (2), liver (3), spleen (4), kidney (5), muscle (6), skin (7) and intestine (8) of the groups of FIG. 7.
Figure 9:
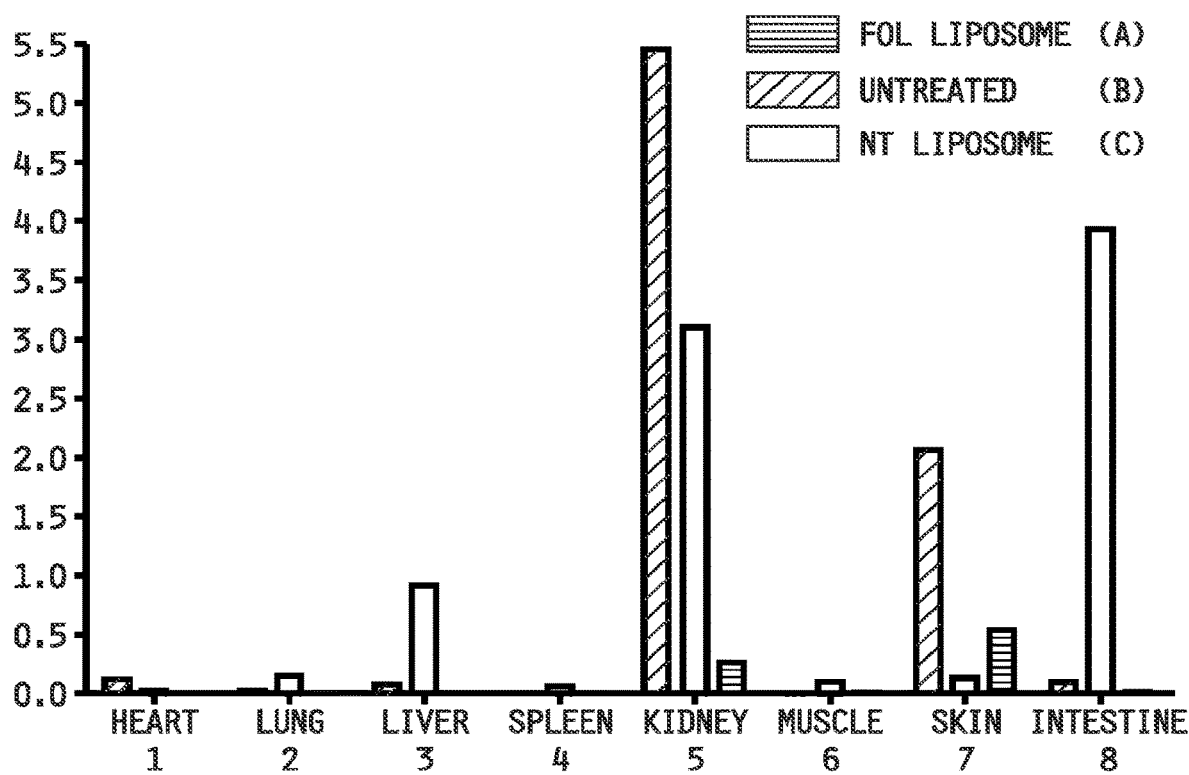

In Therapeutic Example 1, Apo E KO mice were fed a western diet for 3 weeks and dosed as (A) a control (Untreated) group which received a folate-targeted liposomal composition which contained only phospate buffered saline as the entrapped agent, (B) a group (NT Liposome) which received a non-targeted liposomal composition which contained betamethasone as the entrapped agent, and (C) a group (Fol-Liposome) which received a folate-targeted liposomal composition which contained betamethasone as the entrapped agent. The mice were imaged using the folate-receptor targeted, radionuclide conjugate imaging agent EC20 (folate-Tc99m) and the biodistribution of EC20 uptake was determined. The reduction in inflammatory cells imaged by EC20 in the Fol Liposome group compared to the NT Liposome and Untreated groups is demonstrated by the imaged mice (FIG. 7, top) and excised hearts (FIG. 7, bottom), particularly the heart uptake of EC20 (FIG. 8), and biodistribution (FIG. 9).

Figure 10:
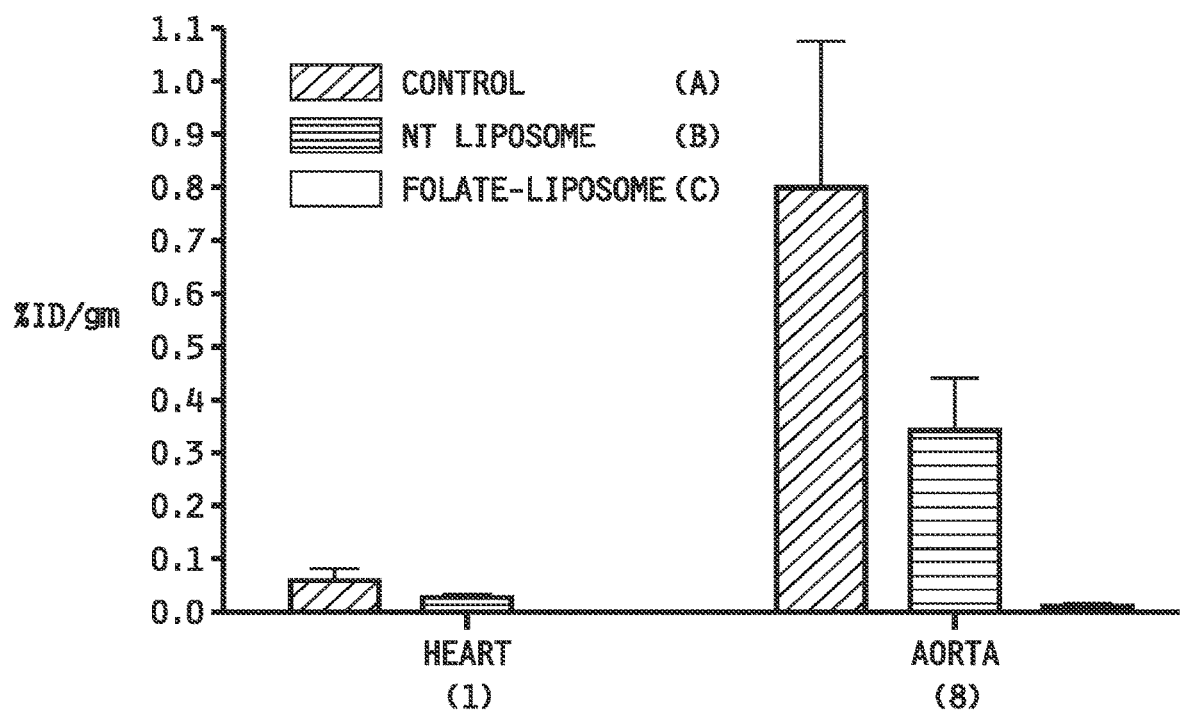
FIG. 10 shows radioisotopic imaging (top) of the hearts (1) and aortas (8) and the biodistribution (bottom) of the organs (heart (1), lung (2), liver (3), intestine (4), kidney (5), spleen (6), muscle (7), aorta (8) and skin (9)) using the folate-receptor targeted, radionuclide conjugate imaging agent EC20 (folate-Tc99m) in Apo E KO mice fed a western diet for 4 weeks and dosed as (A) a control (Untreated) group which received a folate-targeted liposomal composition which contained only phospate buffered saline as the entrapped agent, (B) a group (NT Liposome) which received a non-targeted liposomal composition which contained betamethasone as the entrapped agent, and (C) a group (Fol-Liposome) which received a folate-targeted liposomal composition which contained betamethasone as the entrapped agent.
Figure 10:
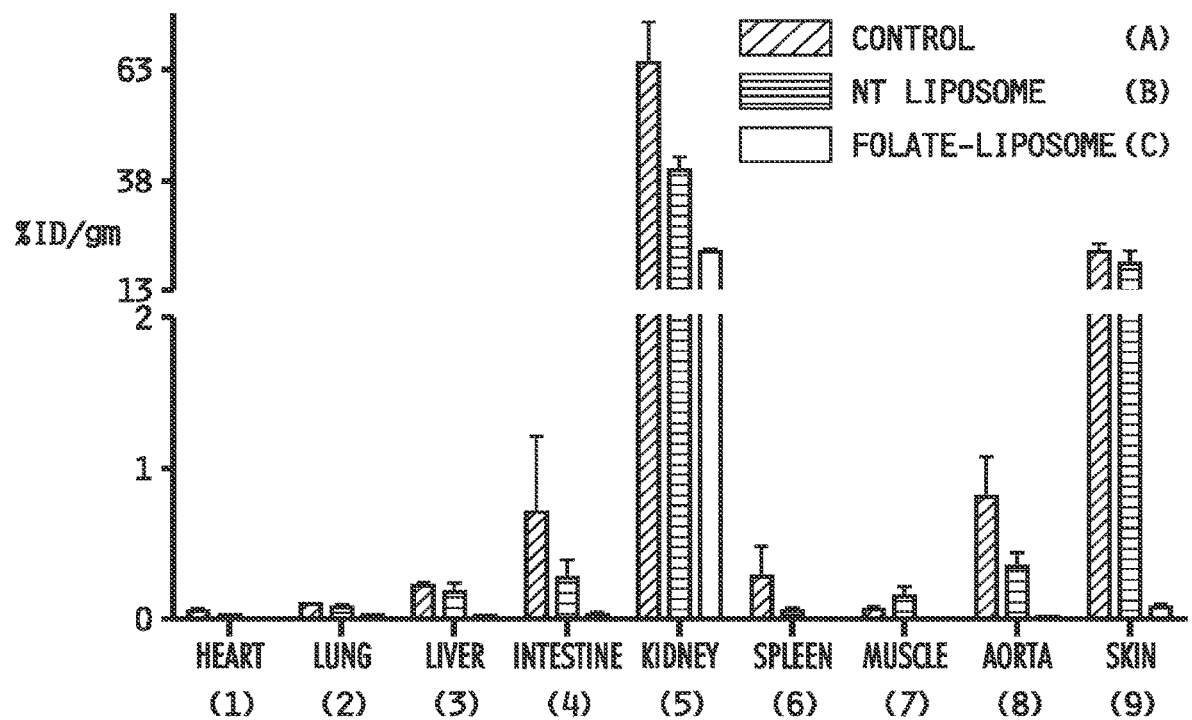

In Therapeutic Example 2, Apo E KO mice were fed a western diet for 4 weeks before dosing as (A) a control (Untreated) group which received a folate-targeted liposomal composition which contained only phospate buffered saline as the entrapped agent, (B) a group (NT Liposome) which received a non-targeted liposomal composition which contained betamethasone as the entrapped agent, and (C) a group (Fol Liposome) which received a folate-targeted liposomal composition which contained betamethasone as the entrapped agent. The mice were imaged using the folate-receptor targeted, radionuclide conjugate imaging agent EC20 (folate-Tc99m) and the biodistribution of EC20 uptake was determined. The reduction in inflammatory cells imaged by EC20 in the Fol Liposome group compared to the NT Liposome and Untreated groups is demonstrated by the measures of EC20 uptake in the hearts and the aortas of the groups FIG. 10 (top); FIG. 10 (bottom) shows the relative biodistribution of EC20 uptake in the organs of the groups.

Imaging Examples 7 through 9 demonstrate the ability of folate-targeted liposomal compositions to deliver entrapped imaging agents to sites of inflammation in other tissues and support the use of folate-targeted liposomal compositions comprising an anti-inflammatory agent as an entrapped agent, as disclosed herein, in the treatment of an inflammatory disease, such as in an inflamed tissue region in the body.

Imaging Example 7 demonstrates (FIG. 11) the ability of the folate-targeted liposomal compositions to deliver entrapped agents to inflamed intestinal tissues, for example in inflammatory bowel disease, such as Crohn's disease or ulcerative colitis, using imaging under the following conditions: (A) DiD-entrapped folate-targeted liposomal composition, (B) DiD-entrapped folate-targeted liposomal composition administered with an excess of folic acid, and (C) non-targeted DiD-entrapped liposomal composition.

Imaging Example 8 demonstrates (FIG. 12) the ability of the folate-targeted liposomal compositions to deliver entrapped agents to inflamed arthritic tissues, for example as in rheumatoid arthritis, using imaging under the following conditions: (A) DiD-entrapped folate-targeted liposomal composition, (B) DiD-entrapped folate-targeted liposomal composition administered with an excess of folic acid, and (C) non-targeted DiD-entrapped liposomal composition.

Imaging Example 8A also demonstrates (FIG. 15) the ability of the folate-targeted liposomal compositions to deliver entrapped agents to inflamed arthritic tissues, for example as in rheumatoid arthritis, using imaging under the following conditions: a non-targeted DiD-entrapped liposomal composition (NT Liposome), a diseased rat imaged with a folate-targeted DiD-entrapped liposomal composition (Fol-Liposome), and a healthy rat with a folate-targeted DiD-entrapped liposomal composition (Healthy).

Imaging Example 9 demonstrates (FIG. 13) the ability of the folate-targeted liposomal compositions to deliver entrapped agents to inflamed skeletal muscle tissues using imaging with (A) a DiD-entrapped folate-targeted liposomal composition, and (B) a DiD-entrapped folate-targeted liposomal composition administered with an excess of folic acid.

Figure 16:
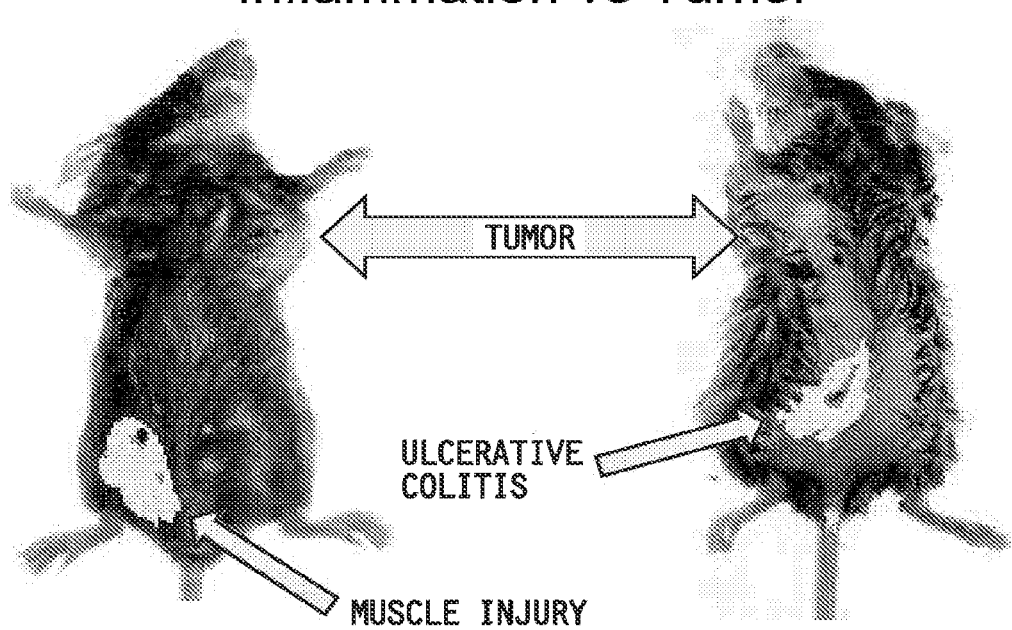
FIG. 16 shows the imaging in mice implanted with (M109) tumors which express the folate receptor at high levels on the surface and concomitantly used in the muscle injury model or the ulcerative colitis model when imaged with a folate-targeted DiD-entrapped liposomal composition (Fol-Liposome).

Imaging Examples 10 and 11 demonstrate (FIG. 16, FIG. 17 and FIG. 18) that the folate-targeted liposomal compositions preferentially deliver entrapped agents to inflammatory tissues as compared to tumors which express a high level of folate receptors on their surface. In addition, the examples demonstrate that the increase in uptake of the folate-targeted liposomal compositions compared to the non-targeted liposomal compositions is greater in the inflammatory tissues than the increase in the tumors.

Imaging Example 12 demonstrates uptake of a folate-targeted dendrimer conjugate conjugated to FITC dye and the competitive inhibition of the uptake by excess folic acid in the cells which express the folate receptor at high levels on the surface.

In Imaging Example 13, ability of a dendrimer conjugate conjugated to Cy5.5 dye to label the atherosclerotic sites in Apo E KO mice fed a western diet before dosing is demonstrated along with a comparison with a non-targeted dendrimer conjugate conjugated to Cy5.5 dye and the competitive blocking of the labeling by competition with a folate-targeted dendrimer conjugate which lacks a conjugated dye. Imaging of both the whole animals (FIG. 22) and the excised aortic arch (FIG. 23) show the labeling of the sites and competitive blocking.

Imaging Example 14 demonstrates (FIG. 24) the ability of a dendrimer conjugate to deliver conjugated agents to inflamed intestinal tissues in an ulcerative colitis model using using imaging with a folate-targeted dendrimer conjugate conjugated to Cy5.5 dye, with a non-targeted dendrimer conjugate conjugated to Cy5.5 dye, and in competition with a folate-targeted dendrimer conjugate which lacks a conjugated dye.

The following examples further illustrate specific embodiments of the invention; however, the following illustrative examples should not be interpreted in any way to are to limit invention. Abbreviations used in the examples include the following: Chol, cholesterol; DCC, dicyclohexylcarbodiimide; DiD, 1,1'-dioctadecyl-3,3,3',3'-tetramethylindodicarbocyanine perchlorate; DIPEA, diisopropylethylamine; DMSO, dimethyl sulfoxide; DSPC, distearoylphosphatidylcholine; DSPE, distearoylphosphatidylethanolamine; EDC, 1-ethyl-3-(3-dimethyl-aminopropyl)carbodiimide hydrochloride; mPEG, methyl capped PEG; MS, mass spectrometry; PBS, phosphate buffered saline; PEG, poly(ethylene glycol).

EXAMPLES

Example Preparations

Exemplary Preparation 1: Preparation of Folate-Targeted Liposomal Compositions

Synthesis of Folate-PEG-NH2

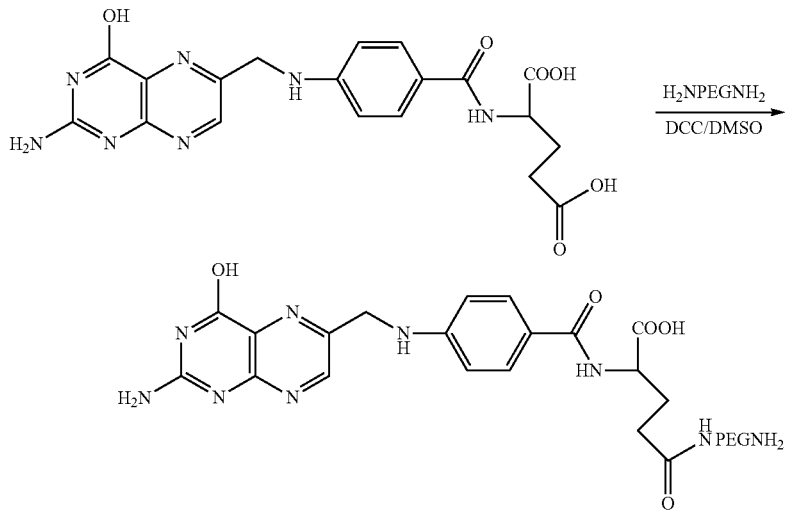

Under $N_2$, Folate-PEG-NH$_2$ is synthesized using 500 mg of NH$_2$PEG$_{3200}$NH$_2$ (PEG-bis amine) with an equimolar quantity of folic acid in 5 mL DMSO containing 1 molar equivalent of DCC or EDC and 10 µl pyridine, triethylamine or DIPEA. The reaction mixture is stirred overnight in the dark at room temperature. The reaction is quenched with water. The by-product urea and the trace amount of unreacted folate and PEG-bis amine are removed by both dialysis and by using a G-15 size exclusion column in deionized water. Folate-PEG-NH$_2$ is analyzed using HPLC with monitoring by absorbance at 363 nm.

Synthesis of N-Succinyl-DSPE

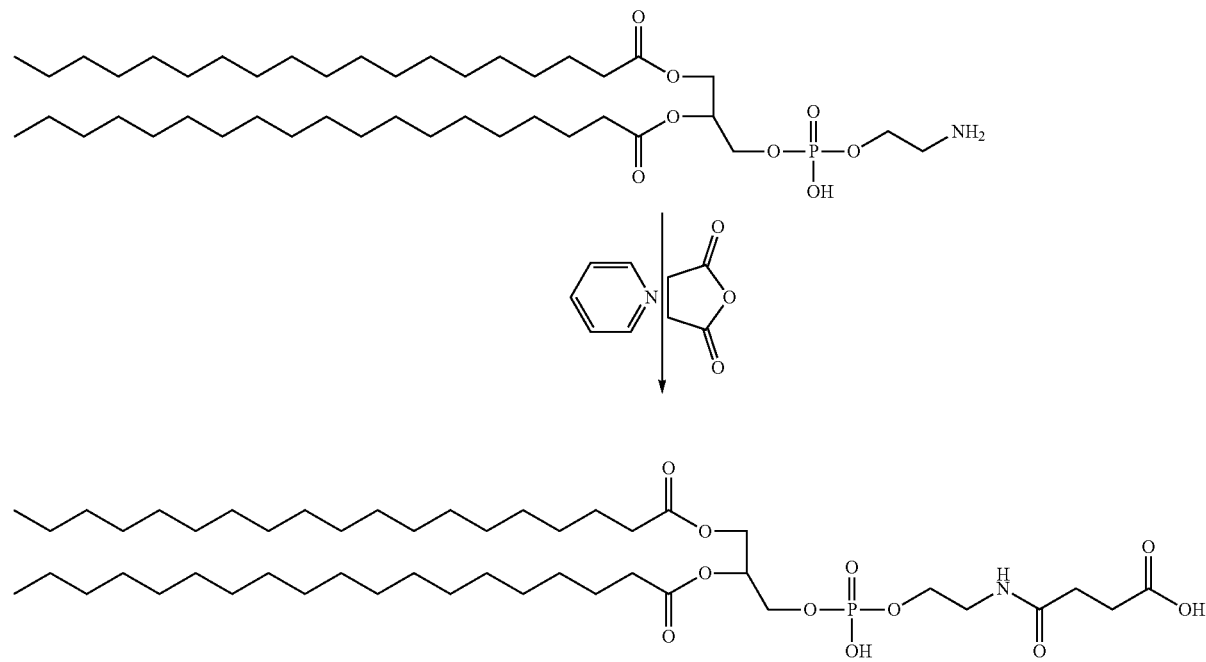

Under $N_2$, N-succinyl-DSPE is synthesized by reacting overnight 1.1 molar equivalent of succinic anhydride with 100 mg DSPE in 5 mL of dry chloroform or dichloromethane containing 10 μL pyridine, triethylamine or DIPEA. The product N-succinyl-DSPE runs as a spot with a higher Rf value (~0.5) than DSPE and is ninhydrin negative on TLC, using chloroform/methanol (3:2) as the solvent phase. The structure of the product N-succinyl-DSPE is confirmed by MS.

Synthesis of Folate-PEG-DSPE

Preparation of Betamethasone-Entrapped Folate-Targeted Liposomal Composition:

126.4 mg of DSPC, 44 mg of cholesterol, 32 mg of mPEG$_{2000}$DSPE and 1 mg of FolatePEG$_{3200}$DSPE are weighed and mixed in a 50 mL round bottom flask. The lipid mixture is dissolved in chloroform before evaporating to dryness in a Rotavapor and kept under vacuum overnight. 200 mg of betamethasone phosphate is weighed and dissolved in 6 mL of phosphate buffered saline. The betamethasone solution is added to the dry lipid film, and the

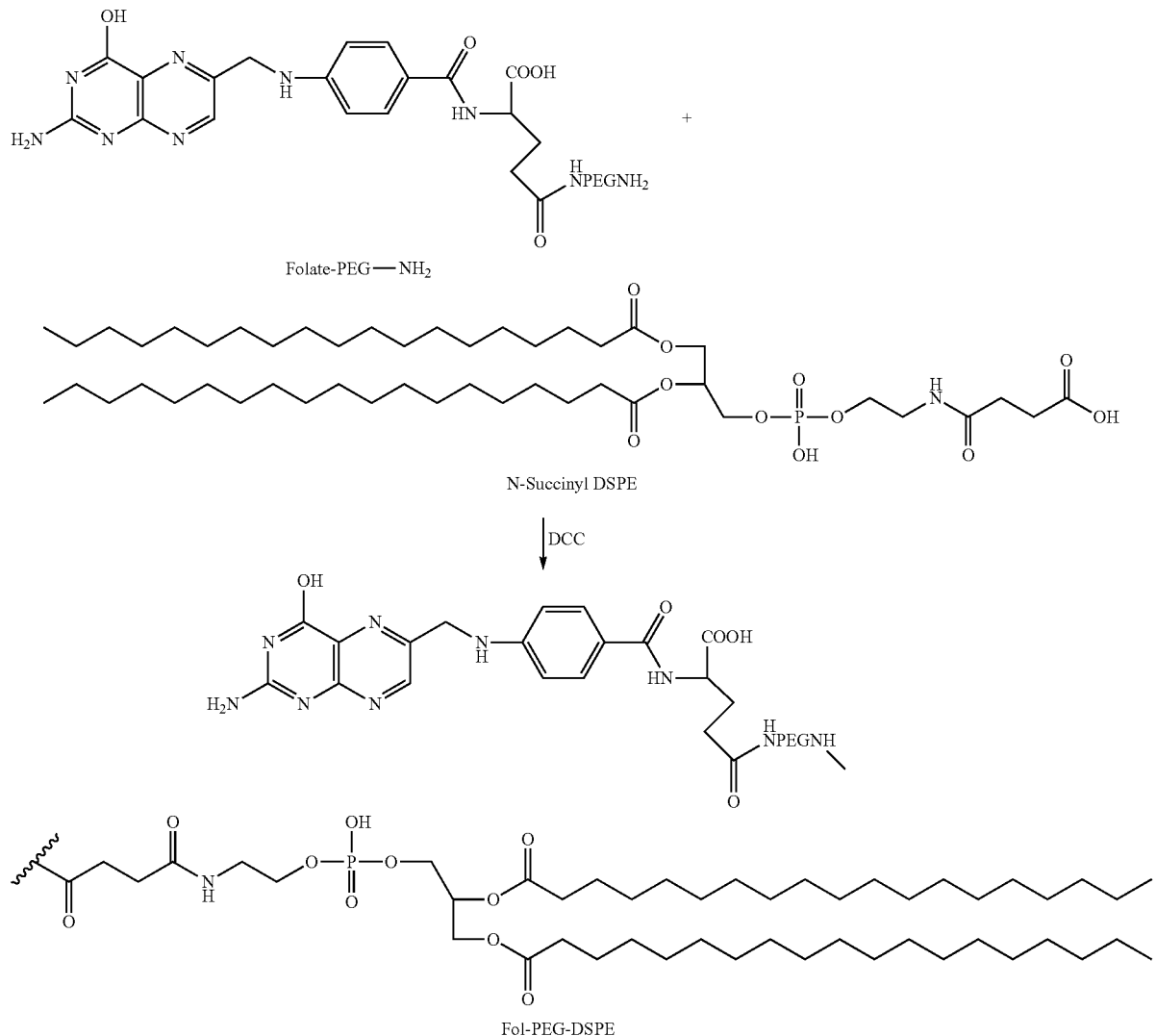

The synthesis of the folate-PEG-DSPE construct is illustrated above. Under nitrogen, N-succinyl-DSPE is dissolved in chloroform and its carboxyl-group is activated by reacting with 0.95 molar equivalent of DCC or EDC. Then an equimolar amount of folate-PEG-DSPE is also dissolved in the above mentioned reaction mixture and the reaction is continued overnight at room temperature. The solvent is then removed under reduced pressure. The unreacted products are then removed from the mixture by membrane dialysis. The product folate-PEG-DSPE is analyzed on a HPLC system chromatography (water/methanol (1.5:1)) using a C-18 reverse phase column.

mixing is further enhanced at 70° C. The mixture is subjected to freeze-thaw cycle 10 times. The liposomal suspension is transferred to an extruder and extruded under nitrogen pressure, 10 times each through 200 nm, 100 nm, and 50 nm pore filters, respectively. The mean particle size of the liposome as determined by light scattering is 60-70 nm.

Preparation of Calcein Entrapped-Folate-Targeted Liposomal Compositions:

In order to prepare calcein entrapped folate-PEG-liposomal compositions, a total mass of 100 mg of the lipid mixture; [DSPC/Chol/mPEG2000-DSPE/folate-PEG-DSPE (56:40:4:0.1) mol %] is dissolved in chloroform and dried to a thin film in a round bottom flask under reduced pressure overnight. The lipid mixture is rehydrated in 10 mM calcein dissolved in PBS (pH 7.4). The resulting lipid suspension is subjected to 10-15 cycles of freezing and thawing. Then 50 nm and 100 nm folate-PEG-liposomes of different size distributions are generated by extruding the lipid suspension 10 times each through polycarbonate membranes having pore sizes of sequentially 800 nm, 400 nm, 200 nm and 100 nm, followed by 50 nm, if needed, respectively. Unentrapped dye is separated using membrane dialysis. Particle size is determined by Dynamic Light Scattering-DynaPro99. Phosphate assay (Steward assay) is performed to determined phospholipid concentration.

Preparation of DiD-Entrapped Folate-Targeted Liposomal Composition (1% Dye with Respect to Phospholipid):

126.4 mg of DSPC, 44 mg of cholesterol, 32 mg of mPEG$_{2000}$DSPE and 1 mg of FolatePEG$_{3200}$DSPE are weighed and mixed in a 50 mL round bottom flask. The lipid mixture is dissolved in chloroform before evaporating to dryness in a Rotavapor and kept under vacuum overnight. 15 µl of 1,1'-dioctadecyl-3,3,3',3'-tetramethylindodicarbocyanine perchlorate (DiD) is added in 6 mL of (pH 7.4) phosphate buffered saline. The dye solution is added to the dry lipid film, and the mixing is further enhanced at 70° C. The mixture is subjected to freeze-thaw-vortex cycle 10 times. The liposomal suspension is transferred to an extruder and extruded under nitrogen pressure, 10 times each through 200 nm, 100 nm, and 50 nm pore filters, respectively. The mean particle size of the liposome as determined by light scattering is about 60 nm.

Preparation of Iobitridol-Entrapped Folate-Targeted Liposomal Compositions:

Lipid mixture consisting of DSPC/Chol/mPEG$_{2000}$DSPE/FolPEG3200DSPE in a 56:40:4:0.1 molar ratio was dissolved in ethanol at 70° C. The ethanol solution was then hydrated with iobitridol (350 mg 1/mL) for 2 h. The suspension of liposomes obtained was submitted to a filtration through 400 nm, 200 nm, 100 nm, and 50 nm (10 cycles each) polycarbonate membranes using an extruder. Liposomes were then dialyzed overnight in a 300K Mw cutoff dialysis bag against PBS solution.

Preparation of Chelated $^{99}$Tc-Entrapped Folate-Targeted Liposomal Compositions by Remote Loading:

(Part 1) Preparation of Folate-Targeted Liposome Encapsulating Glutathione.

Folate-targeted liposomes encapsulating glutathione were prepared using a procedure based on polycarbonate membrane extrusion. Briefly, unilamellar vesicles were prepared from DSPC/Chol/mPEG2000DSPE/FolPEG$_{3200}$DSPE (56:40:4:0.1) by thin film hydration method. Lipids at indicated ratios were dissolved in chloroform, and the solvent was evaporated under vacuum with a stream of N$_2$ gas to remove all organic solvent. The resultant film was then hydrated with 50 mM reduced glutathione in PBS (pH 7.4) at 60° C. with constant stirring. The suspension of liposomes obtained was submitted to a filtration through 400 nm, 200 nm, 100 nm, and 50 nm (10 cycles each) polycarbonate membranes using an extruder. Untrapped residual reduced glutathione was removed by passing the liposome suspension through a Sephadex G50 column.

(Part 2) Radiolabeling of Tc-99m into Liposomes

The commercially available kit of HMPAO, hexamethylpropylene amine oxime (Ceretec®, UK) was labeled with Tc-99m. The kit was reconstituted with 15 mCi sodium pertechnetate in 0.9% NaCl solution at room temperature for 8 minutes. The 99mTc-HMPAO complex was then mixed with the preformed liposome (part1) and incubated at 37° C. with intermittent vortexing for 30 minutes. Uncapsulated 99mTc-HMPAO was removed by gel filtration on a Sephadex G50 column using PBS as an eluent.

Exemplary Preparation 2: Preparation of NonTargeted (NT) Liposomal Compositions

For comparison experiments, liposomal compositions are prepared as disclosed for the preparation of the corresponding folate-targeted liposomal compositions, except the folate-PEG-DSPE conjugate is omitted.

Exemplary Preparation 3: Preparation of Folate-Targeted Dendrimer Conjugates

An exemplary preparation of a folate-targeted dendrimer conjugate conjugated to a fluorescent dye (Cy 5.5 NHS or FITC) using a Dendritech Generation 3 (G3) poly(amido amine) (PAMAM), denoted as "Dendrimer," having a molecular weight of 6,909 Daltons, a measured diameter of 36 Å, and 32 surface primary amino groups follows: On the average, each resulting dendrimer conjugate contains six folate-PEG residues, ten mPEG residues and two Cy 5.5 or FITC residues.

Synthesis of Folate-PEG-NH$_2$

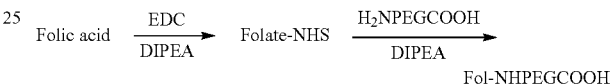

Under N$_2$, Folate-PEG-COOH is synthesized using 500 mg of NH$_2$PEGCOOH (Mw' 3400) with equimolar quantity of folic acid in 5 mL DMSO containing 1 molar equivalent of dicyclohexylcarbodiimide (DCC) or 1-ethyl-3-(3-dimethylaminopropyl) carbodiimide hydrochloride (EDC) and 104 pyridine, triethylamine or diisopropylethylamine (DIPEA). The reaction mixture is stirred overnight in the dark at room temp. The reaction is quenched with H$_2$O. The trace amount of unreacted folate is also removed by both dialysis and G-15 size exclusion column in dH$_2$O. Folate-PEG-COOH is analyzed using HPLC by absorbance at 363 nm.

Synthesis of Folate-PEG-Dendrimer

Figure 20:
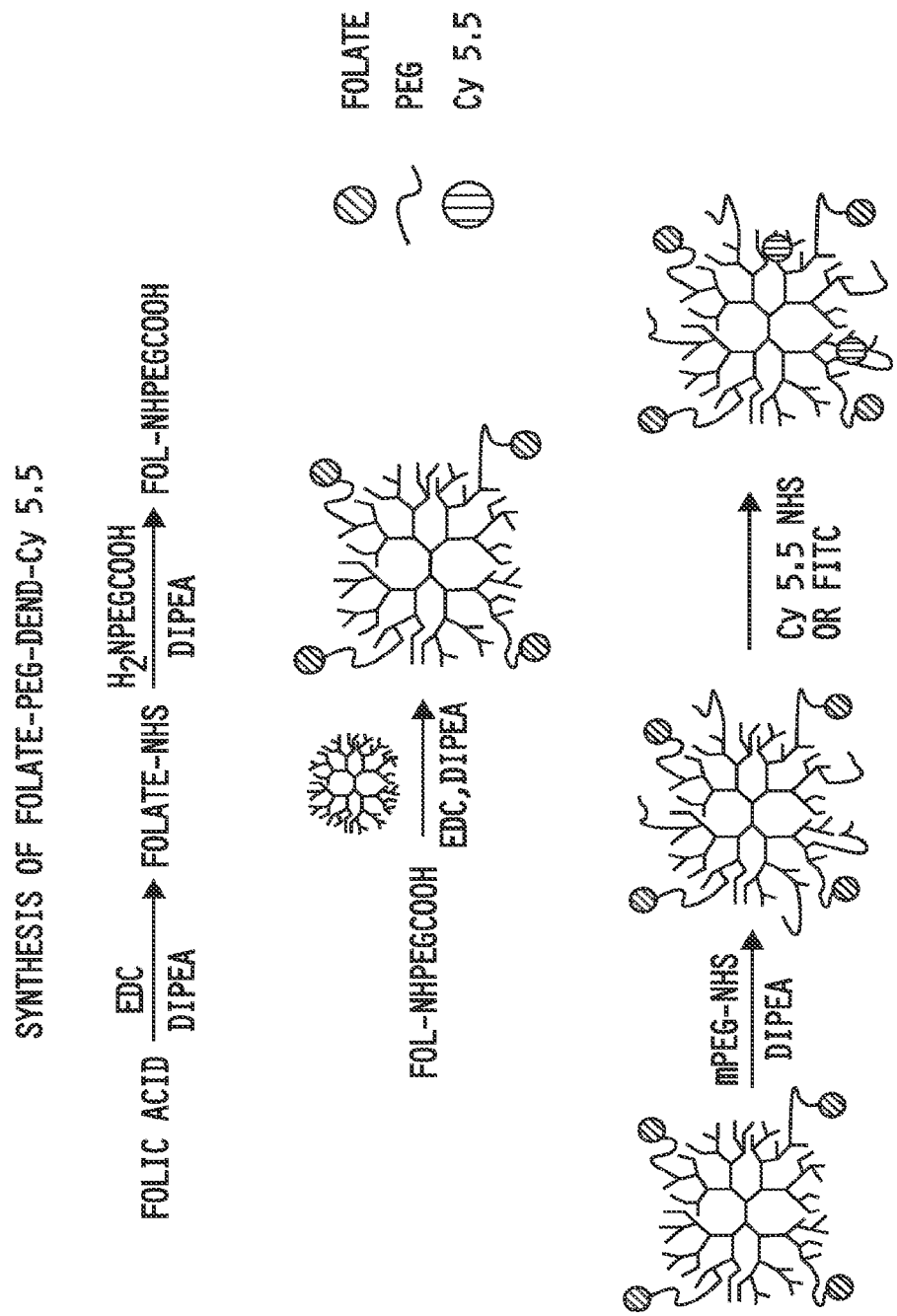
FIG. 20 shows a synthetic scheme for the preparation of a folate-targeted dendrimer conjugate conjugated to a dye. Folate-targeted dendrimer conjugates conjugated to active agents, such as anti-inflammatory agents, may be prepared similarly.

Under N$_2$, FolatePEG-Dendrimer is synthesized by reacting overnight 6 molar equivalent of FolNHPEGCOOH and EDC (6 eq) with Dendrimer (1 eq) in 5 mL of dry DMSO containing 10 µL pyridine, triethylamine or DIPEA, as shown in FIG. 20. The trace amount of unreacted materials is also removed by both dialysis and G-15 size exclusion column in dH$_2$O. Folate-PEG-Dendrimer is analyzed using UV/Vis and IR.

Synthesis of Folate-PEG-Dendrimer with mPEG

The synthesis of the pegylated folate-PEG-Dendrimer construct is illustrated above, briefly under nitrogen, mPEG-NHS (10 eq, Mw ~2000) is dissolved in dry DMSO, and 40 µL pyridine, triethylamine or DIPEA is added, as shown in FIG. 20. Then 1 equivalent amount of folate-PEG-Dendrimer is also dissolved with the above mentioned reaction mixture overnight at room temperature. The unreacted mixture is then removed by membrane dialysis, confirmed by UV/Vis and IR.

Loading of FITC or Cy 5.5 into Folate-PEG-Dendrimer:

In order to prepare folate-PEG-Dendrimer loaded with dye (FITC or Cy 5.5), 1 equivalent of Folate-PEG-Dendrimer and Cy 5.5 NHS (2 eq) or FITC (2 eq) are dissolved in dry DMSO. 40 µL pyridine, triethylamine or DIPEA is added, as shown in FIG. 20. The reaction is carried out overnight at room temperature. The unreacted mixture is then removed by membrane dialysis. The remaining product is freeze dried and confirmed by UV/Vis and IR.

Exemplary Preparation 4: Preparation of Non-Targeted Dendrimer Conjugates

For non-targeted dendrimer conjugates, the coupling with FolNHPEGCOOH is omitted.

Exemplary Preparation 5: Preparation of Folate-Targeted Dendrimer Conjugates without Conjugated Dye For competition studies, the step of coupling with a dye is omitted to provide folate-dendrimer conjugates.

THERAPEUTIC EXAMPLES

Figure 7:
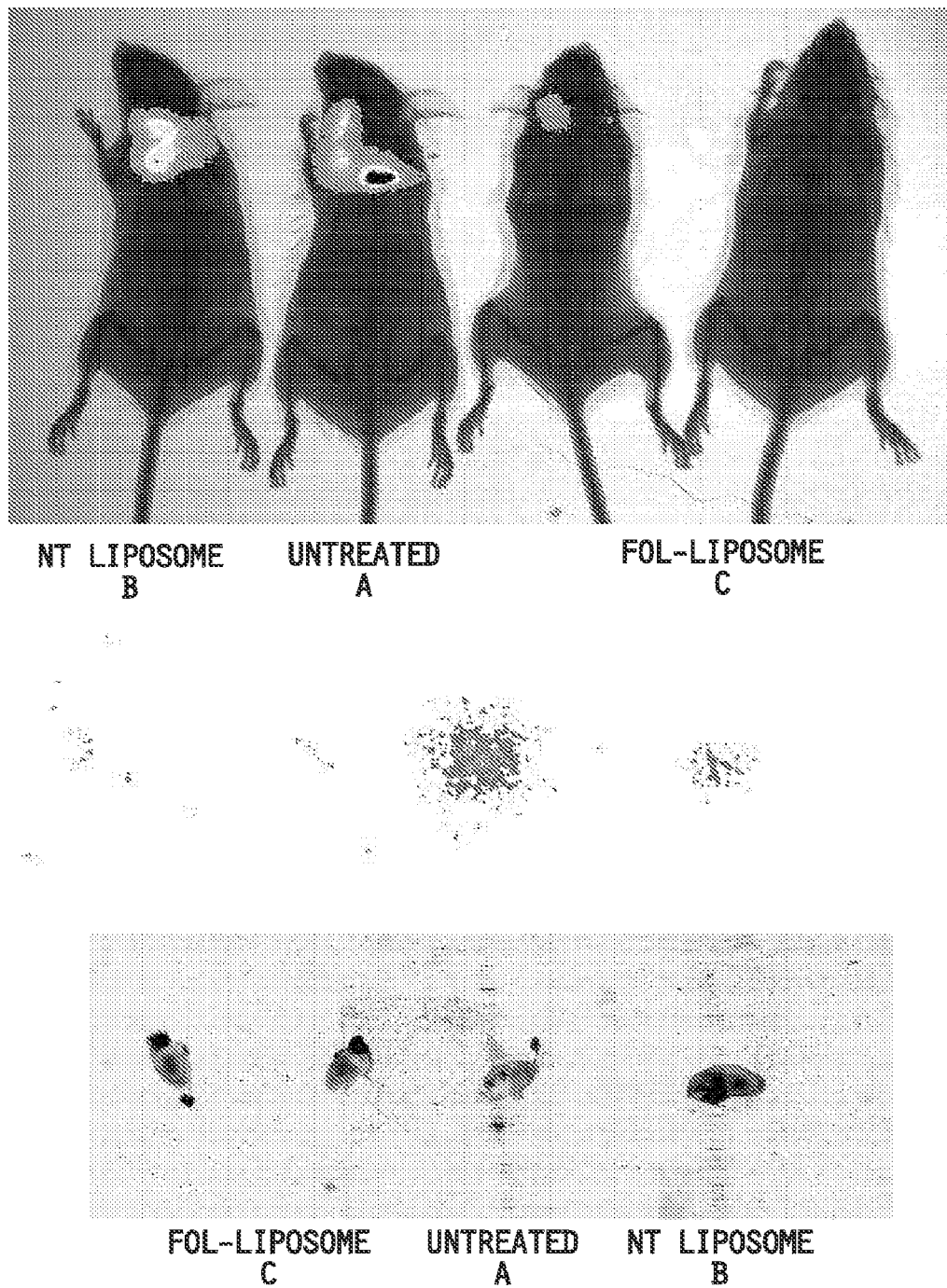
FIG. 7 shows radioisotopic imaging of the whole animal (top) and excised hearts (bottom) using the folate-receptor targeted, radionuclide conjugate imaging agent EC20 (folate-Tc99m) in Apo E KO mice fed a western diet for three weeks and dosed as (A) a control (Untreated) group which received a folate-targeted liposomal composition which contained only phospate buffered saline as the entrapped agent, (B) a group (NT Liposome) which received a non-targeted liposomal composition which contained betamethasone as the entrapped agent, and (C) a group (Fol-Liposome) which received a folate-targeted liposomal composition which contained betamethasone as the entrapped agent.

Therapeutic Example 1. Treatment with a Betamethasone-Entrapped Folate-Targeted Liposomal Composition in a 3-Week Model of Atherosclerosis in the Apo E Knock-Out Mouse Three groups of Apo E KO mice (Untreated (A), NT Liposome (B) and Fol Liposome (C)) were fed with a western diet for 3 weeks. The Fol Liposome Treated group was injected i.v., twice per week, with a betamethasone-entrapped folate-targeted liposomal composition. The NT Liposome group was injected similarly with a non-targeted betamethasone-entrapped liposomal composition. The Untreated group was similarly injected with a folate-targeted liposomal composition with only encapsulated phosphate buffer solution. One day after the last liposome injection, all groups were injected with the folate-receptor targeted, radio-nuclide conjugate imaging agent EC20 (folate-Tc99m) before radioisotopic imaging and monitoring of EC20 uptake. The images are shown in FIG. 7 (top) of the whole animals and in FIG. 7 (bottom) of the hearts of the three groups. The relative EC 20 uptake in the heart for each of the three groups is shown if FIG. 8. The relative EC 20 uptake in various organs is shown in FIG. 9.

Therapeutic Example 2. Treatment with a Betamethasone-Entrapped Folate-Targeted Liposomal Composition in a 4-Week Model of Atherosclerosis in the Apo E Knock-Out Mouse Three groups (Untreated (A), NT Liposome (B) and Fol-Liposome (C)) of Apo E KO mice (3 mice per group) were fed a western diet for 4 weeks. The Fol Liposome group was injected i.v. twice per week with a folate-targeted betamethasone-entrapped liposomal composition. The NT Liposome group was similarly injected with a non-targeted betamethasone-entrapped liposomal composition. The Untreated group was similarly injected with a folate-targeted liposomal composition with only encapsulated phosphate buffer solution. One day after the last liposome injection, the groups were injected with the folate-receptor targeted, radio-nuclide conjugate imaging agent EC20 (folate-Tc99m) before radioisotopic imaging and monitoring of EC20 uptake. FIG. 10 (top) shows the relative EC20 uptake of the hearts and the aortas of the groups; FIG. 10 (bottom) shows the relative biodistribution of EC20 uptake in the organs of the groups.

IMAGING EXAMPLES

Imaging Example 1. Uptake of Calcein from a Calcein-Entrapped Folate-Targeted Liposomal Composition by Rat Peritoneal Cells in a Thioglycolate-Induced Inflammation Model 30 g of dehydrated brewer thioglycolate medium powder was dissolved in 1 L of deionized water and autoclaved for 25 minutes at 15 pounds pressure (124° C.). The autoclaved medium was kept in the dark under sterile conditions at room temperature for at least 3 months before use.

Thioglycolate recruited macrophages were isolated by peritoneal lavage 3 days after intraperitoneal injection of 3.0 mL 3% sterile medium.

After 3 days, the Lewis rats were sacrificed by $CO_2$ asphyxiation, and the peritoneal macrophages were harvested by injecting 60 mL of PBS into the peritoneal cavity. After centrifugal separation of the cells collected in the PBS, the cells were resuspended into Eppendorf tubes with FDRPMI 1640 medium. The medium was replaced with fresh medium containing Folate-targeted liposome encapsulating dye (DiD or calcein). For competition studies, excess free folic acid is preintroduced to the peritoneal medium for 30 min before addition of folate targeted liposome. For control, empty folate targeted liposome (PBS) were used. All media were incubated for 2 h at 37° C. The cells were washed 3 times with PBS and resuspended in fresh PBS. The cell bound fluorescence was analyzed using flow cytometry.

In FIG. 14 are shown the results of the flow cytometry for control and calcein-entrapped folate-targeted liposomal compositions in the presence and absence of excess free folic acid.

Figure 1:
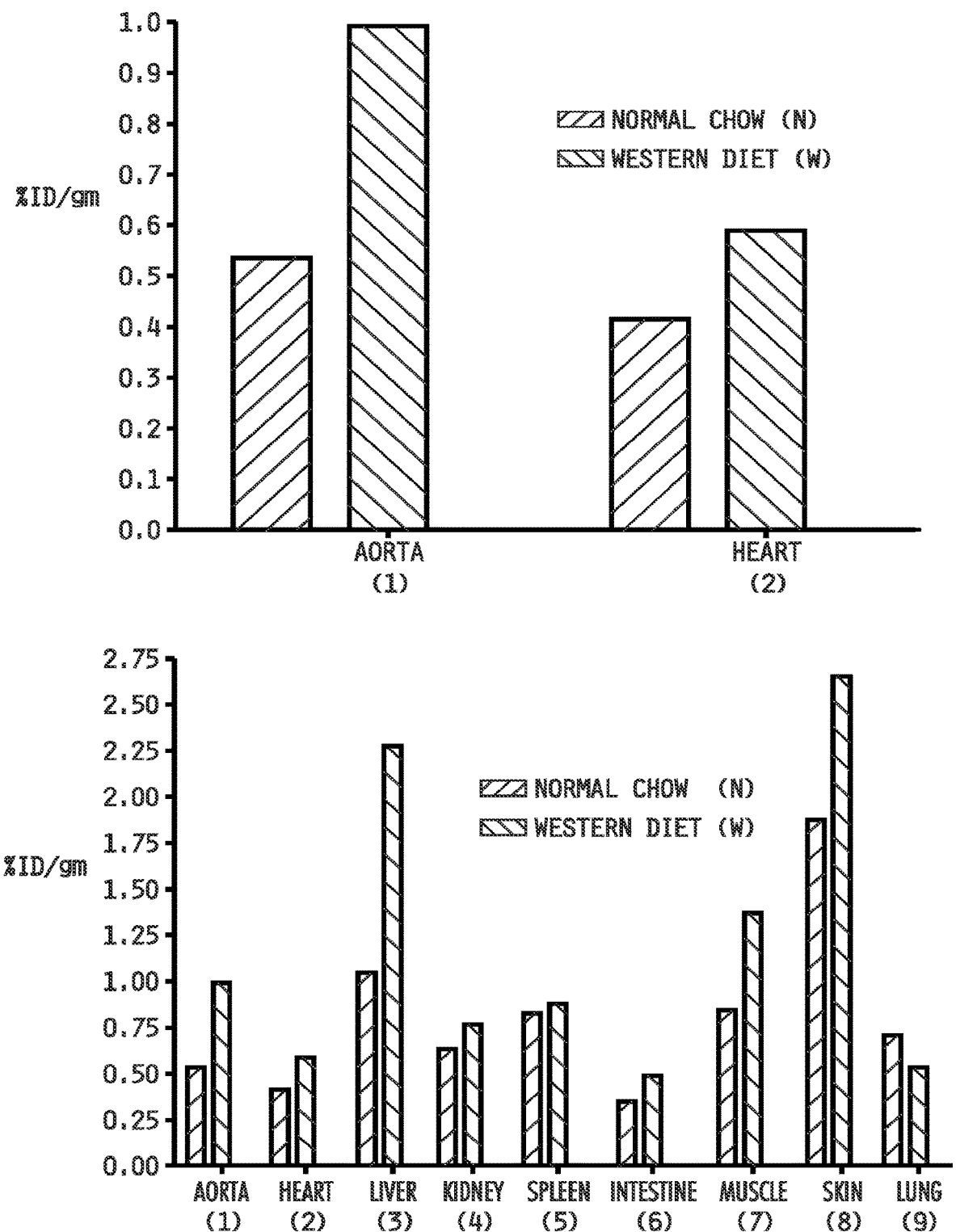
FIG. 1 (top) shows the relative biodistribution of uptake of $^3$H-cholesterol labeled folate-targeted liposomes in the aortas (1) and hearts (2) of Normal Chow (N) and Western Diet (W) mice; the biodistribution in a number of organs (aorta (1), heart (2), liver (3), kidney (4), spleen (5), intestine (6), muscle (7), skin (8) and lung (9)) is shown in FIG. 1 (bottom).

Imaging Example 2. Labeling and Biodistribution of Atherosclerotic Lesions in Apo E Knock Out Mice Fed Normal and Western Diets One set of Apo E KO mice (Normal Chow) was fed a normal diet and one set of Apo E KO mice (Western Diet) was fed a high fat western diet for two weeks. Each mouse then received a folate-targeted liposome composition (2 mg total phospholipid, i.v) containing 10 µCi $^3$H cholesterol-oleoyl-ether. The animals were sacrificed 24 h later, and organs were removed. Tissue samples were solubilized using Soluene 350 (1 mL/100 mg tissue) at 60° C. for 48 h. Tissue solutions were then bleached to uniform color using 30% hydrogen peroxide, followed by 6 mL Hionic-Fluor scintillation cocktail. 1 mL of tissue solution was counted on scintillation counter. The relative biodistribution of uptake of the labeled liposomes in the aorta and hearts of Normal Chow and Western Diet mice is shown in FIG. 1 (top); the biodistribution in a number of organs is shown in FIG. 1 (bottom).

In the following examples, when DiD is the imaging agent, approximately 50 nm DiD-entrapped liposomes of DSPC/Chol/mPEG$_{2000}$DSPE/FolPEG$_{3400}$DSPE (56:40:4: 0.1) were used, along with the corresponding non-targeted liposomes. For competition studies excess 0.1 mM folic acid was used. Administration was i.p.

Figure 2:
FIG. 2 shows whole body imaging of the atherosclerotic sites in Apo E KO mice fed a western diet for one week using a folate-targeted liposomal composition, with the entrapped fluorescent dye DiD, preinjection (top) and 2 hours post injection (bottom) in the absence (left) and presence (right) of pre-administered folic acid. The scale shows low (bottom) to high (top) intensity of fluorescence.
Figure 3:
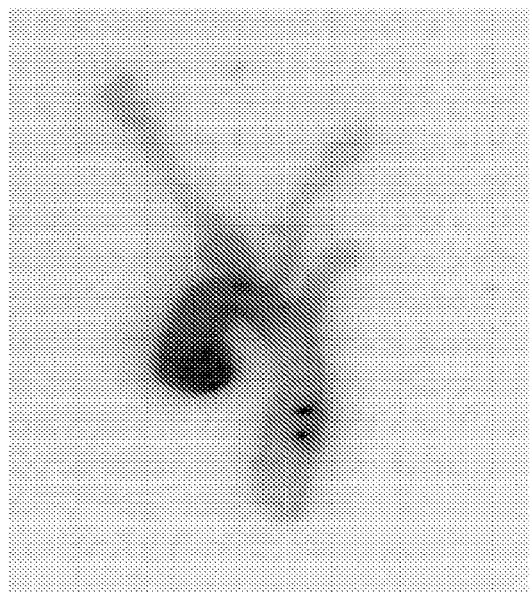
FIG. 3 shows the imaging of the atherosclerotic sites in the aortic arch in Apo E KO mice fed a western diet for one week using a folate-targeted liposomal composition, with the entrapped fluorescent dye DiD. Atherosclerotic plaques showed a 5-fold increase in mean fluorescence.
Figure 3:
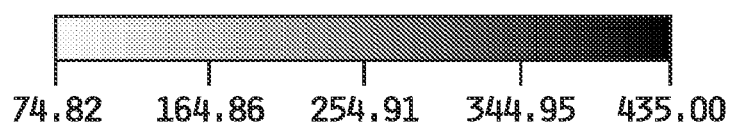

Imaging Example 3. Imaging with a DiD-Entrapped Folate-Targeted Liposomal Composition in a 1-Week Model of Atherosclerosis in the Apo E Knock-Out Mouse Apo E knockout mice are fed with western diet for 1 week. After 7 days, mice received the DiD-entrapped folate-targeted liposomal composition (fol-PEG-liposome-DiD) (0.2 µmol lipid) i.p. (total volume injected: 100 µl) in each mouse. For competition studies, mice were pre-administered free folic acid (50 µl) before i.p injection of DiD liposome. Images were taken 2 h postinjection. The images are shown in FIG. 2 and FIG. 3.

Figure 4:
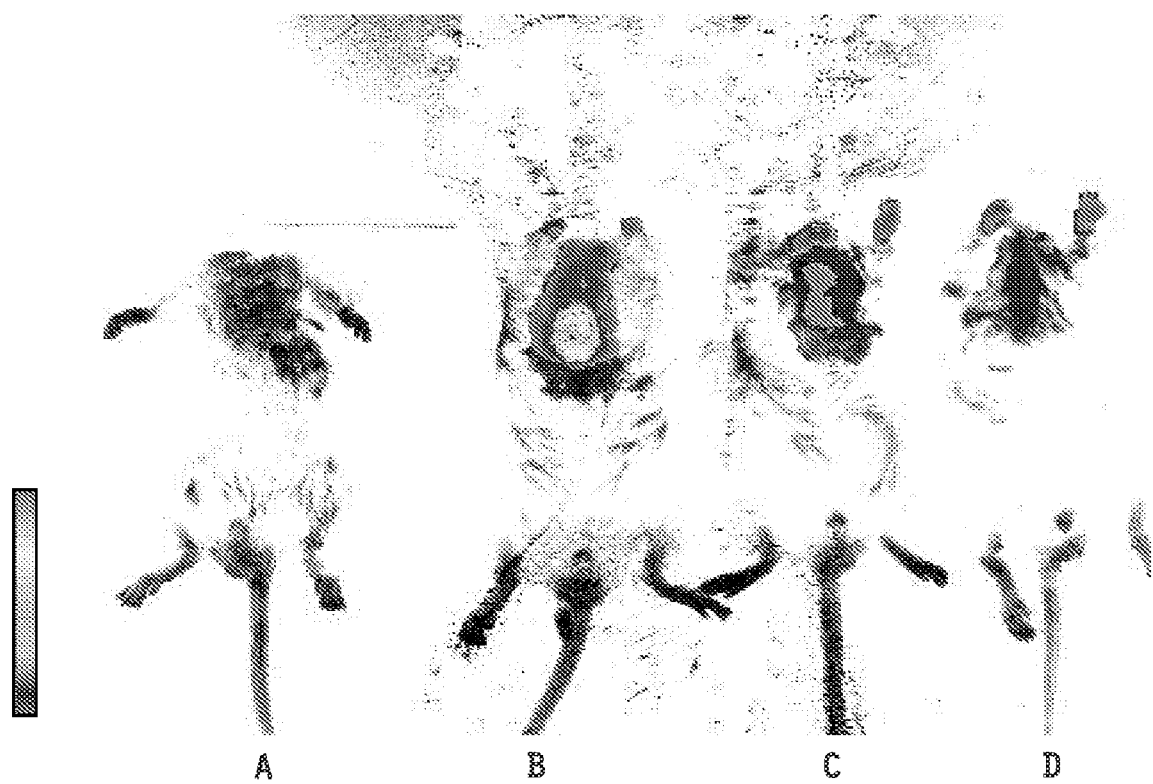
FIG. 4 shows whole body imaging of the atherosclerotic sites in Apo E KO mice fed a western diet for four weeks before imaging under four conditions: (A) control with no imaging agent, (B) DiD-entrapped folate-targeted liposomal composition, (C) non-targeted DiD-entrapped liposomal composition, and (D) DiD-entrapped folate-targeted liposomal composition administered with an excess of folic acid.

Imaging Example 4. Imaging with a DiD-Entrapped Folate-Targeted Liposomal Composition in a 4-Week Model of Atherosclerosis in the Apo E Knock-Out Mouse Apo E knockout mice are fed with western diet for 4 weeks. DiD-entrapped liposomes were administered. The animals were imaged after 4 hours. The images are shown in FIG. 4.

Imaging Example 5. Imaging with Iobitridol-Entrapped Folate-Targeted Liposomal Composition in a Model of Atherosclerosis in the Apo E Knock-Out Mouse An Apo E KO mouse (7 weeks old) was subjected to i.p. injection of the iobitridol-entrapped folate-targeted liposomal composition described above ($3.0 \times 10^{-6}$ mol total lipids). The mouse was imaged by X-ray: preinjection, T=2, 3, 24, 48 hours interval. The images are shown in FIG. 5.

Figure 6:
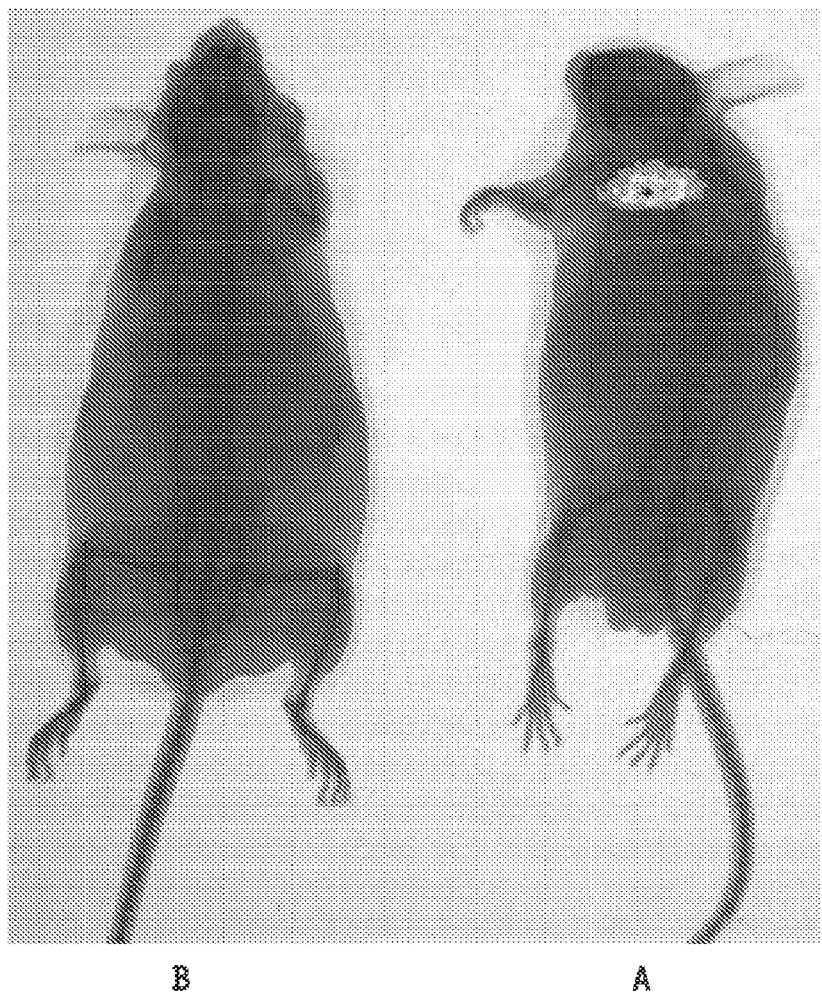
FIG. 6 shows radioisotopic imaging in Apo E KO mice fed a western diet for four weeks before dosing using a $^{99}$Tc-entrapped folate-targeted liposomal composition, administered either alone (A) or with an excess of folic acid (B).

Imaging Example 6. Imaging with a $^{99}$Tc-Entrapped Folate-Targeted Liposomal Composition in an 8-Week Model of Atherosclerosis in the Apo E Knock-Out Mouse Two groups of Apo E KO mice were fed with western diet for 8 weeks. One group of Apo E KO mice (competition group) was subjected to 0.1 mM free folic acid thru i.p. injection. After 1 hour, i.p. injection of the $^{99}$Tc-entrapped folate-targeted liposomal composition was preformed on both groups of mice. Images were taken 4 hours postinjection. The images are shown in FIG. 6.

Figure 11:
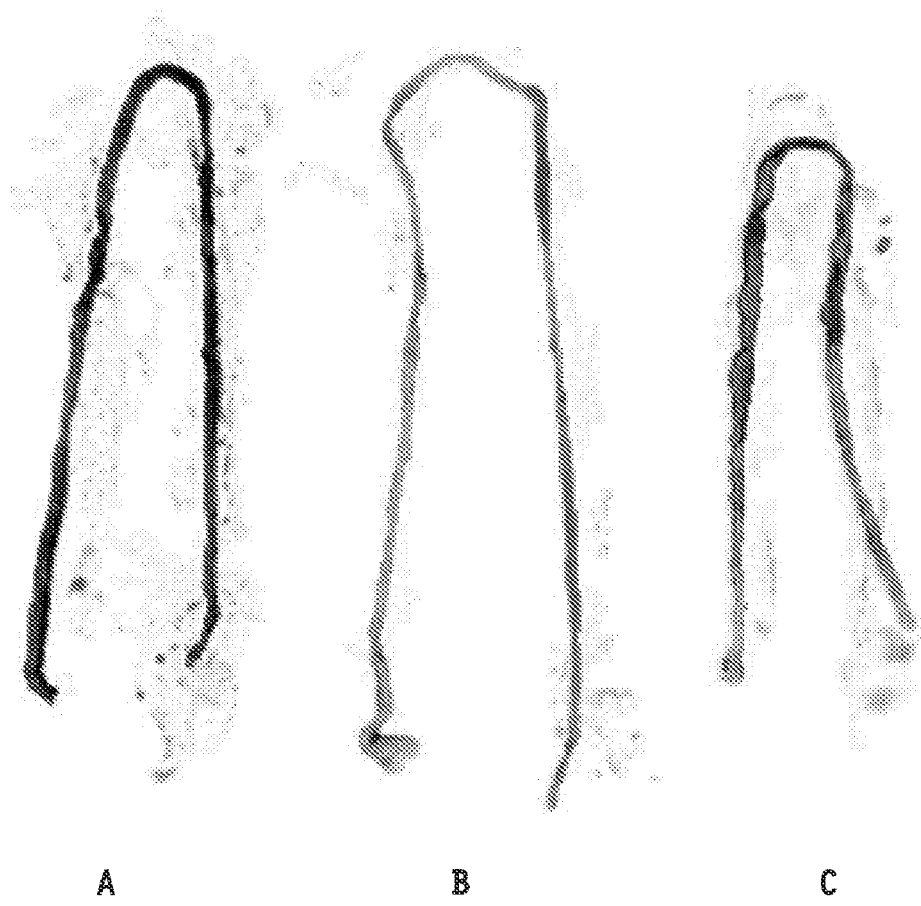
FIG. 11 shows the imaging of the intestines of mice in an intestinal inflammation model using imaging with (A) a DiD-entrapped folate-targeted liposomal composition, (B) a DiD-entrapped folate-targeted liposomal composition administered with an excess of folic acid, and (C) a non-targeted DiD-entrapped liposomal composition.

Imaging Example 7. Imaging with a DiD-Entrapped Folate-Targeted Liposomal Composition in a Murine Intestinal Inflammation (Ulcerative Colitis) Model Three C57 mice were fed with a 2% dextran sodium sulfate for 7 days. After 7 days, DiD-entrapped liposomes were administered. Intestines were removed and imaged after 4 h. The images are shown in FIG. 11.

Figure 12:
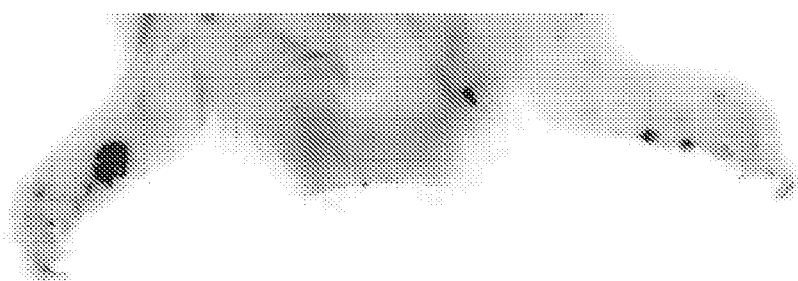
FIG. 12 shows the imaging of the paws of rats in an arthritis model using imaging with (A) a DiD-entrapped folate-targeted liposomal composition, (B) a DiD-entrapped folate-targeted liposomal composition administered with an excess of folic acid, and (C) a non-targeted DiD-entrapped liposomal composition.
Figure 12:
Figure 12:
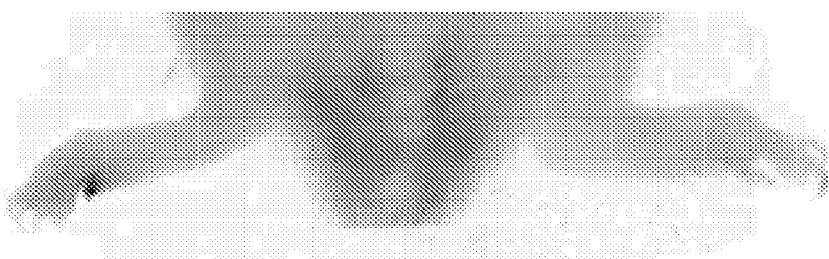
Figure 12:
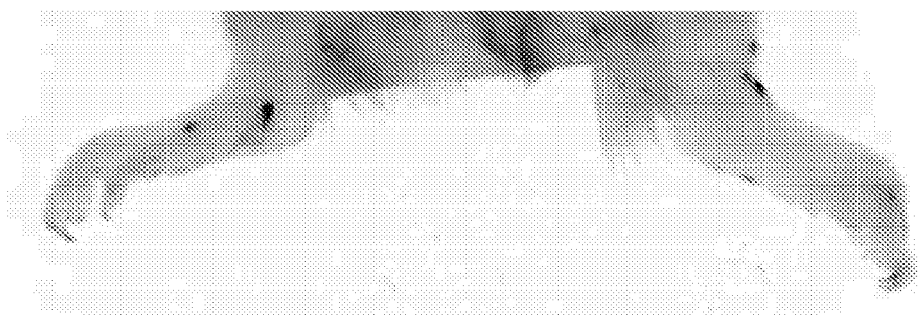

Imaging Example 8. Imaging with a DiD-Entrapped Folate-Targeted Liposomal Composition in an Adjuvant-Induced Arthritis Model in the Rat Adjuvant-induced arthritis (AIA) in Lewis rats was induced by injection of *butyricum* (0.15 mg) into a hind paw. After 17 days, DiD-entrapped liposomes were administered. The hind paws of the rats were imaged. The images are shown in FIG. 12.

Figure 15:
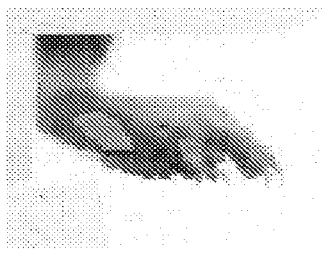
FIG. 15 shows the imaging of the paws of rats in an arthritis model showing a diseased rat imaged with a non-targeted DiD-entrapped liposomal composition (NT Liposome), a diseased rat imaged with a folate-targeted DiD-entrapped liposomal composition (Fol-Liposome), and a healthy rat with a folate-targeted DiD-entrapped liposomal composition (Healthy).
Figure 15:
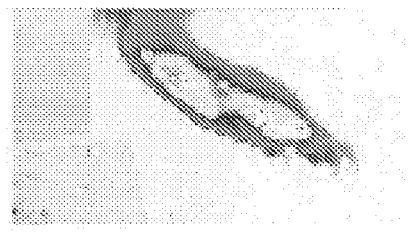
Figure 15:

Imaging Example 8A. Imaging with a DiD-Entrapped Folate-Targeted Liposomal Composition in an Adjuvant-Induced Arthritis Model in the Rat Adjuvant-induced arthritis (MA) in Lewis rats was induced by injection of heat killed *Mycoplasma butyricum* (0.5 mg), suspended in mineral oil (5 mg/mL), on day 1 into the left hind foot of Lewis rats. Disease was allowed to progress for 17 days. 100% of animals developed arthritis as evidenced by gross swelling in the injected paw and progressive swelling in all extremities. DiD-entrapped liposomes were administered (i.v.). The hind paws of the rats were imaged after 12 hours. The images are shown in FIG. 15.

Figure 13:
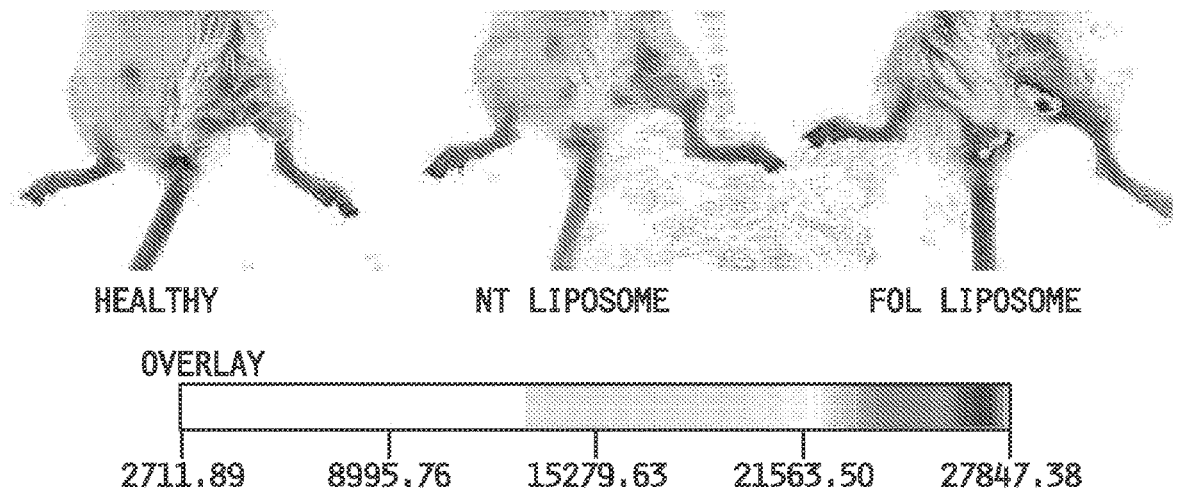
FIG. 13 shows the imaging of mice in an inflammatory muscle injury model showing a healthy mouse imaged with a folate-targeted DiD-entrapped liposomal composition (Healthy), a cardiotoxin treated mouse imaged with a non-targeted DiD-entrapped liposomal composition (NT Liposome), and a cardiotoxin treated mouse imaged with a folate-targeted DiD-entrapped liposomal composition (Fol Liposome). The scale shows low (left) to high (right) intensity of uptake of the label.
Figure 13:
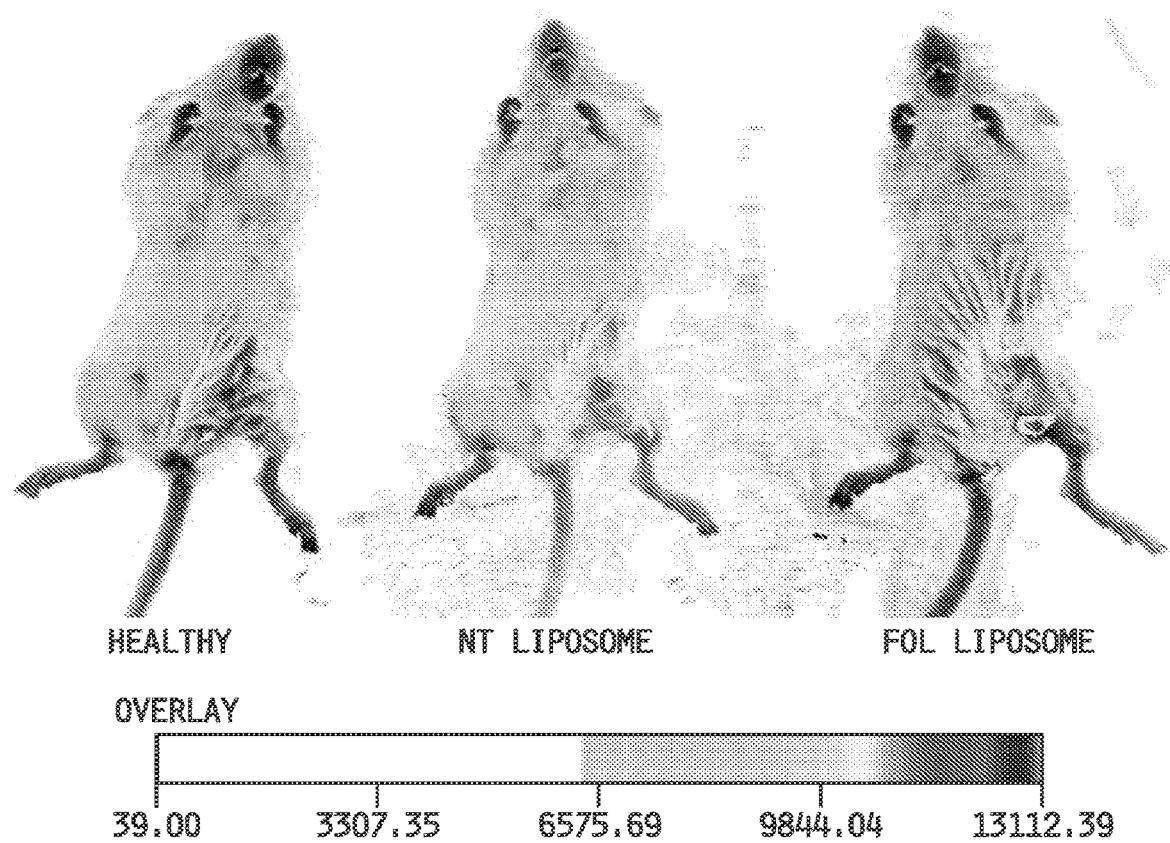

Imaging Example 9. Imaging with a DM-Entrapped Folate-Targeted Liposomal Composition in a Cardiotoxin-Induced Muscle Injury Model in the Rat Four mice were injected with 100 µl, of a 10 µM solution of a cardiotoxin (from *Naja mossambica mossambica*), and two mice were used as controls. Four days later, the two healthy mice were injected with folate-targeted DiD-entrapped liposomes, as were two mice with cardiotixin-induced muscle injury (chosen randomly). The two remaining cardiotoxin-injected mice (chosen randomly) were treated with non-targeted DiD-entrapped liposome. 300 µg of phospholipid were injected per mouse. The dye used was 1% DiD. Images were taken eight hours after a tail vein injection. The images of three of the mice are shown in FIG. 13.

Figure 17:
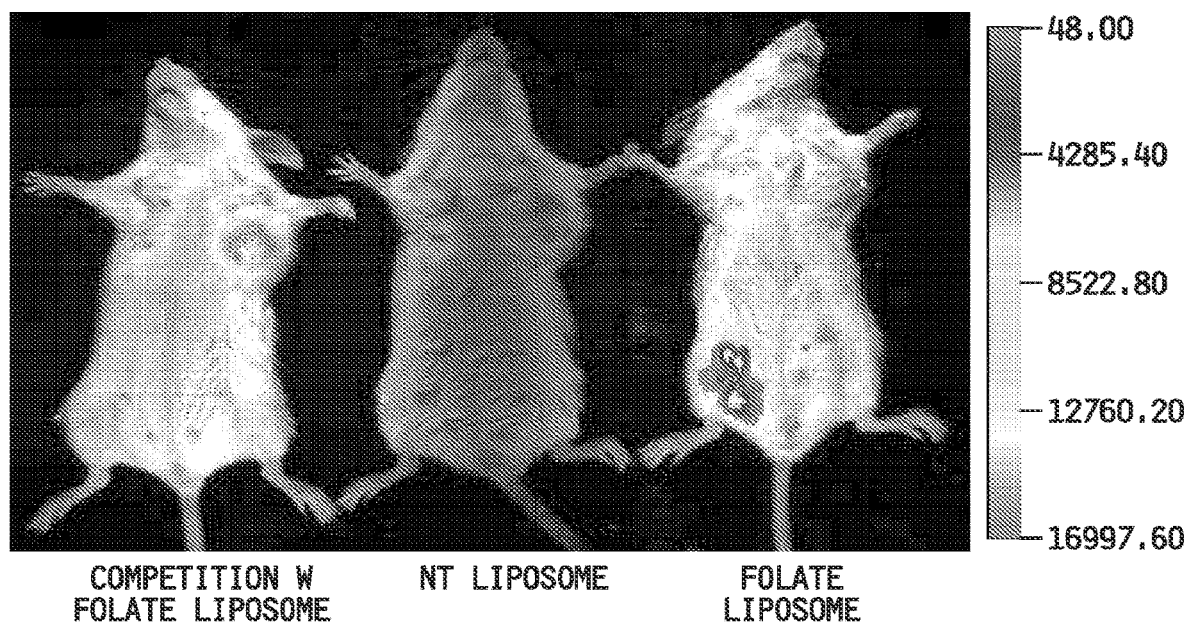
FIG. 17 shows the imaging in mice implanted with (M109) tumors which express the folate receptor at high levels on the surface and concomitantly used in the muscle injury model when imaged with a non-targeted DiD-entrapped liposomal composition (NT Liposome), with a folate-targeted DiD-entrapped liposomal composition (Fol-Liposome), and with empty folate-targeted liposome (injected empty folate-targeted liposome first, then dosed with a folate-targeted DiD-entrapped liposomal composition) (Competition with Folate Liposome).

Imaging Example 10. Imaging with a DiD-Entrapped Folate-Targeted Liposomal Composition in a Cardiotoxin-Induced Muscle Injury Model in in Mice Implanted with M109 Tumor Cells One million M109 cells were injected subcutaneously into a shoulder of Balb-C mice. On day 14 post tumor cell inoculation, the mice were injected in the opposite thigh with 100 µL of a 10 µM solution of a cardiotoxin (from *Naja mossambica mossambica*). Four days later, on day 18, mice were treated i.v. with a non-targeted DiD-entrapped liposomal composition (NT Liposome), with a folate-targeted DiD-entrapped liposomal composition (Fol-Liposome), and with empty folate-targeted liposome (injected empty folate-targeted liposome first, then dosed with a folate-targeted DiD-entrapped liposomal composition) (Competition with Folate Liposome). The mice were imaged 8 hours later. The images of the mice are shown in FIG. 17.

Figure 18:
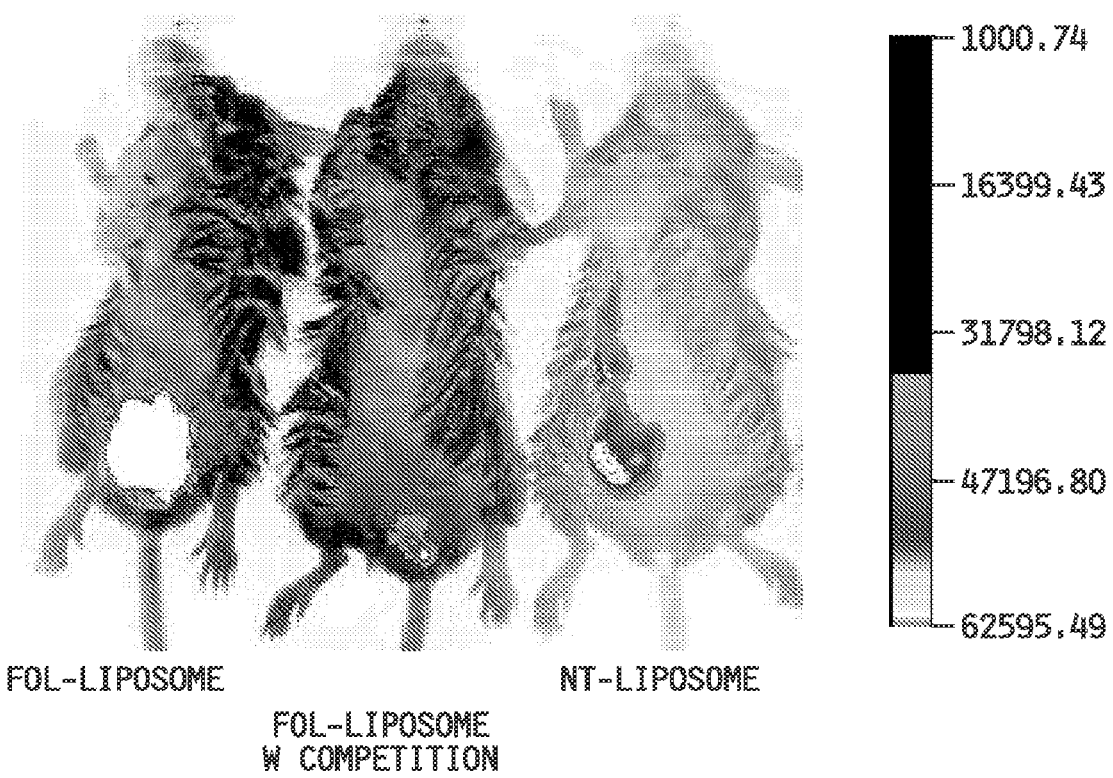
FIG. 18 shows the imaging in mice implanted with (M109) tumors which express the folate receptor at high levels on the surface and concomitantly used in an intestinal inflammation model when imaged with a non-targeted DiD-entrapped liposomal composition (NT Liposome), with a folate-targeted DiD-entrapped liposomal composition (Fol-Liposome), and with empty folate-targeted liposome (injected empty folate-targeted liposome first, then dosed with a folate-targeted DiD-entrapped liposomal composition) (Fol-Liposome with Competition).
Figure 19:
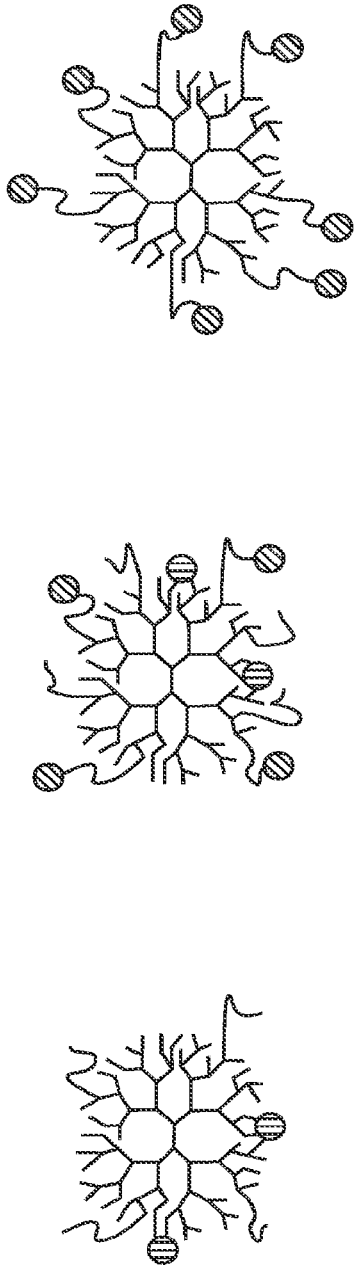
FIG. 19 shows schematically the types of dendrimer conjugates used in the imaging studies.

Imaging Example 11. Imaging with a DiD-Entrapped Folate-Targeted Liposomal Composition in a Murine Intestinal Inflammation (Ulcerative Colitis) Model in Mice Implanted with M109 Tumor Cells One million M109 cells were injected subcutaneously into a shoulder of Balb-C mice. On day 11 post tumor cell inoculation, the mice were administered 2% dextran sodium sulfate (DSS) for 5 days. The mice were then treated i.v. with a non-targeted DiD-entrapped liposomal composition (NT Liposome), with a folate-targeted DiD-entrapped liposomal composition (Fol-Liposome), and with empty folate-targeted liposome (injected empty folate-targeted liposome first, then dosed with a folate-targeted DiD-entrapped liposomal composition) (Folate Liposome W Competion). The mice were imaged 8 hours later. The images of the mice are shown in FIG. 18.

Imaging Example 12. Uptake of Folate-Targeted Dendrimer Conjugate by Cells which Express the Folate Receptor at High Levels on the Surface (Control) and in the Presence of a Folate-Targeted Dendrimer Conjugate Conjugated to FITC Dye (FolDendFITC) Alone and in the Presence of Excess Folic Acid (FolDendFITC w Excess Folic Acid)

Figure 21:
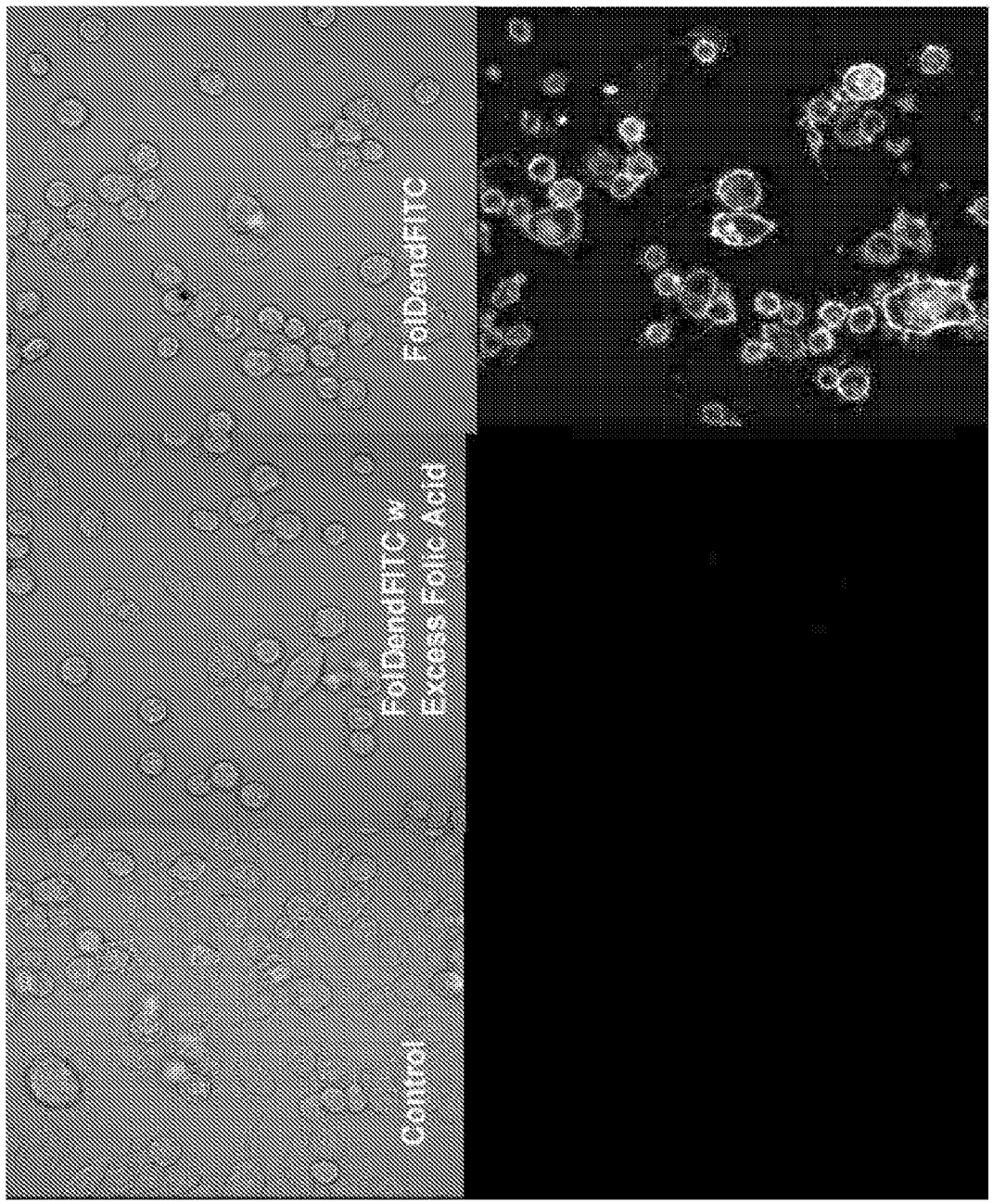
FIG. 21 shows imaging of cells which express the folate receptor at high levels on the surface (control) and in the presence of a folate-targeted dendrimer conjugate conjugated to FITC dye (FolDendFITC) alone and in the presence of excess folic acid (FolDendFITC w Excess Folic Acid).

Raw cells are plated in each well and treated with 10 µL of the indicated dendrimers (1.0 mg/mL). After 1 hour of incubation, confocal imaging is carried out. The images are shown in FIG. 21.

Imaging Example 13. Imaging in the Apo E Knock-Out Mouse Model of Atherosclerosis with a Folate-Targeted Dendrimer Conjugate Conjugated to Cy5.5 Dye (FolDend(G3)Cy5.5), with a Non-Targeted Dendrimer Conjugate Conjugated to Cy5.5 Dye, and in Competition with a Folate-Targeted Dendrimer Conjugate which Lacks a Conjugated Dye (FolDend(G3)Cy5.5 W Competion)

Figure 22:
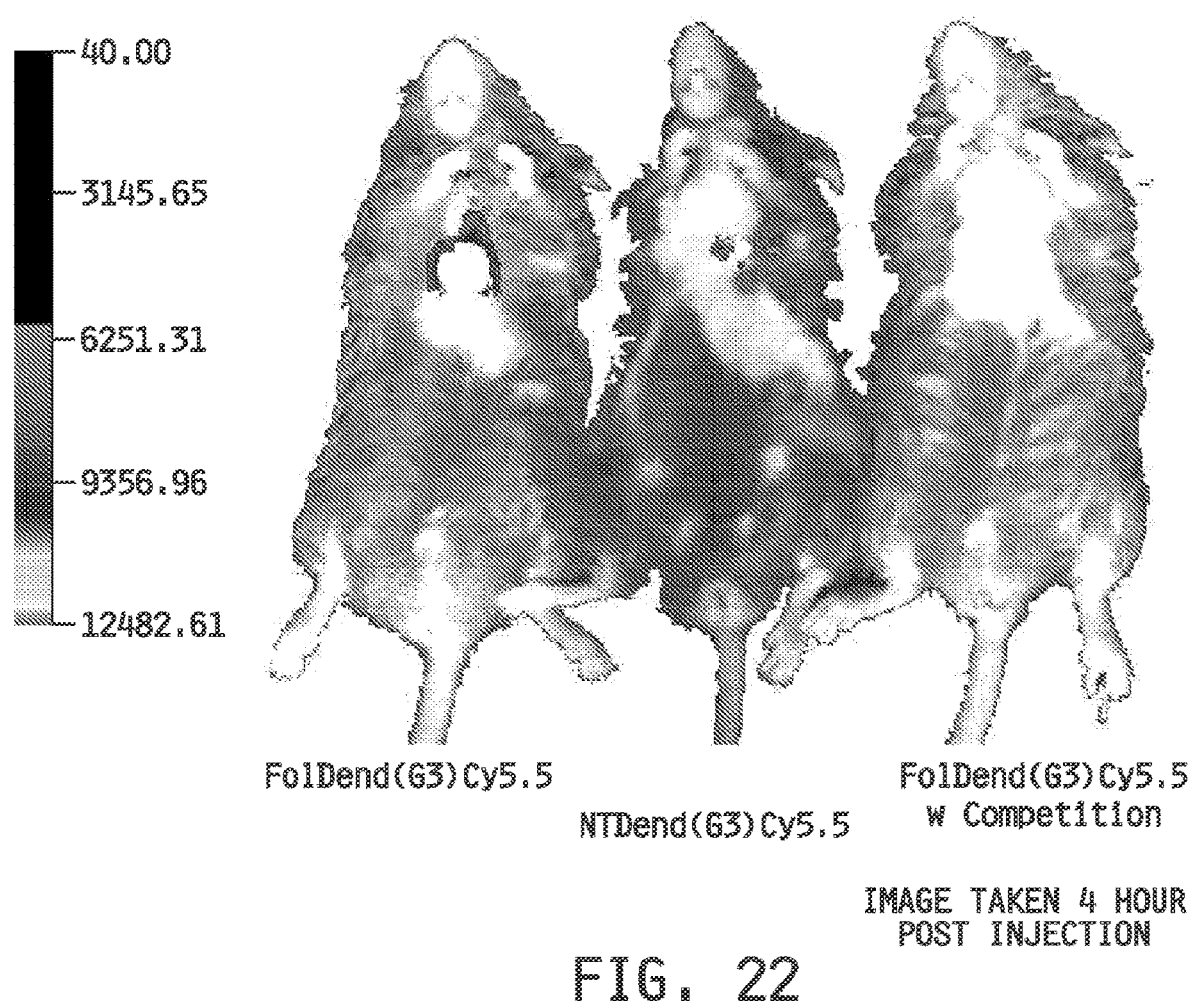
FIG. 22 shows whole body imaging of the atherosclerotic sites in Apo E KO mice fed a western diet with a folate-targeted dendrimer conjugate conjugated to Cy5.5 dye (Fol-Dend(G3)Cy5.5), with a non-targeted dendrimer conjugate conjugated to Cy5.5 dye, and in competition with a folate-targeted dendrimer conjugate which lacks a conjugated dye (FolDend(G3)Cy5.5 W Competion).
Figure 23:
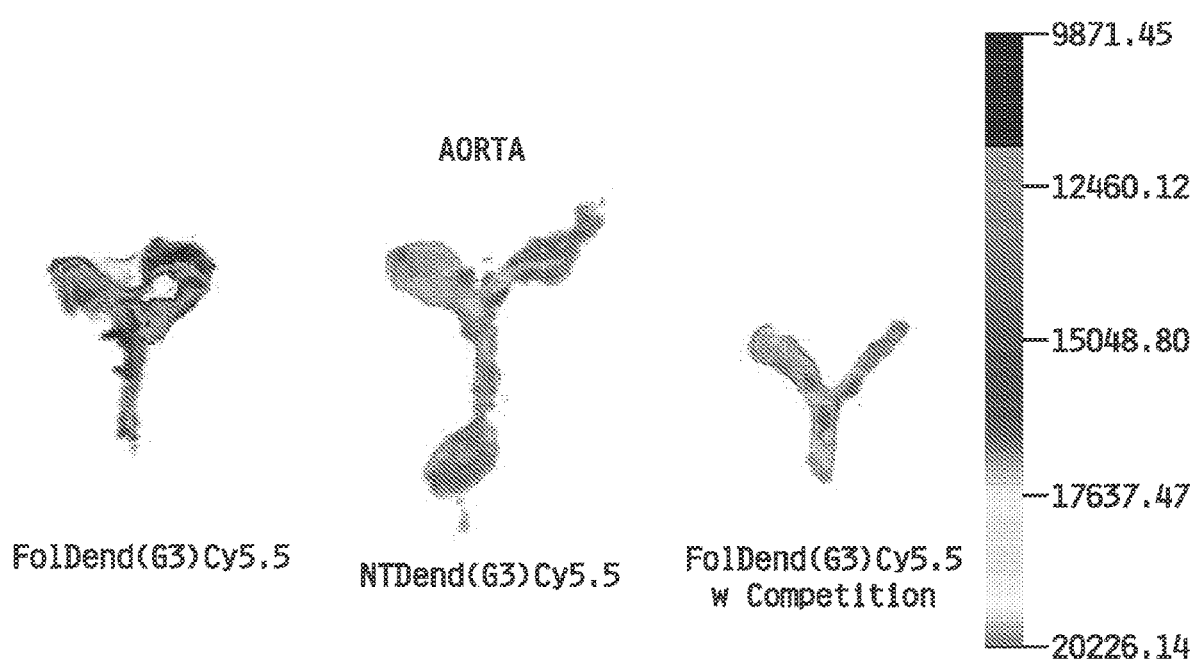
FIG. 23 shows the imaging of the atherosclerotic sites in the aortic arch in Apo E KO mice fed a western diet with a folate-targeted dendrimer conjugate conjugated to Cy5.5 dye (FolDend(G3)Cy5.5), with a non-targeted dendrimer conjugate conjugated to Cy5.5 dye, and in competition with a folate-targeted dendrimer conjugate which lacks a conjugated dye (FolDend(G3)Cy5.5 W Competion).

Apo E knockout mice are fed with western diet are treated with the indicated dendrimer conjugates and imaged 4 hours post injection. The images are shown in FIG. 22. The images of the excised aortas are shown in FIG. 23.

Imaging Example 14. Imaging in a Murine Intestinal Inflammation (Ulcerative Colitis) Model with a Folate-Targeted Dendrimer Conjugate Conjugated to Cy5.5 Dye (FolDend(G3)Cy5.5), with a Non-Targeted Dendrimer Conjugate Conjugated to Cy5.5 Dye, and in Competition with a Folate-Targeted Dendrimer Conjugate which Lacks a Conjugated Dye (FolDend(G3)Cy5.5 W Competion)

C57 mice were fed with a 2% dextran sodium sulfate, and the indicated dendrimer conjugates were administered. The mice were imaged after 6 h. The images are shown in FIG. 24.

What is claimed is:

1. A folate-targeting dendrimeric conjugate comprising
   (i) a folate-targeting conjugate comprising a folate-targeting ligand (Fol), which is a folic acid residue or an analog or derivative thereof,
   (ii) a hydrophilic coating, and
   (iii) an anti-inflammatory agent;
   wherein
   (a) the anti-inflammatory agent is conjugated to the folate-targeting dendrimeric conjugate;
   (b) the folate-targeting conjugate is present at about 12-25% of the dendrimeric termini;
   (c) the hydrophilic coating is present at about 25-40% of the dendrimeric termini; and
   (d) the anti-inflammatory agent is present at about 3-13% of the dendrimeric termini.

2. The folate-targeting dendrimeric conjugate of claim 1, wherein the hydrophilic coating is a polyethylene glycol (PEG), a polylactic acid (PLA), a polyglycolic acid (PGA) or a polyvinyl alcohol (PVA).

3. The folate-targeting dendrimeric conjugate of claim 1, wherein the conjugated anti-inflammatory agent is an anti-inflammatory steroid.

4. The folate-targeting dendrimeric conjugate of claim 1, wherein the conjugated anti-inflammatory agent is a drug useful in the treatment of rheumatoid arthritis or the anti-inflammatory agent is an antiproliferative agent, an immunomodulator, or an immunosuppressant.

5. A method of treatment of an inflammatory disease in a subject in need thereof, comprising administering an effective amount of the folate-targeting dendrimeric conjugate of claim 1.

6. A pharmaceutical composition comprising the folate-targeting dendrimeric conjugate of claim 1 and at least one pharmaceutically acceptable carrier or excipient.

7. A composition comprising a folate-targeting dendrimeric conjugate comprising
   (i) a folate-targeting conjugate comprising a folate-targeting ligand (Fol), which is a folic acid residue or an analog or derivative thereof,
   (ii) a hydrophilic coating, and
   (iii) and an imaging agent or a visualizing agent;
   wherein
   (a) the imaging agent or the visualizing agent is conjugated to the folate-targeting dendrimeric conjugate;
   (b) the folate targeting conjugate is present at about 12-25% of the dendrimeric termini;
   (c) the hydrophilic coating residue is present at about 25-40% of the dendrimeric termini; and
   (d) wherein the composition further comprises at least one pharmaceutically acceptable carrier or excipient.

8. A method of using the composition of claim 7 for diagnosis or monitoring the treatment of an inflammatory disease in an inflamed tissue region in the body of a subject in need thereof.

9. A kit comprising the composition of claim 7 and instructions for diagnosis or monitoring the treatment of an inflammatory disease.

10. A kit comprising the folate-targeting dendrimeric conjugate of claim 1, or a pharmaceutical composition thereof, and an imaging agent for the inflammatory condition.

11. The composition of claim 7, wherein the imaging agent is a fluorescent dye.

12. The composition of claim 11, fluorescent dye is 1,1'-dioctadecyl-3,3,3',3'-tetramethylindodicarbocyanine perchlorate (DiD), calcein or fluorescein.

13. The composition of claim 7, wherein the visualizing agent is a contrast agent for X-ray, MRI (magnetic resonance imaging) or ultrasound.

14. The composition of claim 13, wherein the visualizing agent is a contrast agent for X-ray.

15. The composition of claim 14, wherein the contrast agent is iobitridol.

16. The composition of claim 7, wherein the imaging agent a radionuclide.

17. The composition of claim 7, wherein the radionuclide is an isotope of gallium, indium, copper, technitium or rhenium.

18. The composition of claim 7, wherein the hydrophilic coating is a polyethylene glycol (PEG), a polylactic acid (PLA), a polyglycolic acid (PGA) or a polyvinyl alcohol (PVA).

* * * * *